(12) United States Patent
Huddleston

(10) Patent No.: US 11,744,566 B2
(45) Date of Patent: Sep. 5, 2023

(54) APPARATUS AND METHODS FOR MINIMALLY INVASIVE TRANSCATHETER TRANSAPICAL PUNCTURE, IMAGING, AND CATHETER ALIGNMENT TECHNIQUES

(71) Applicant: Tendyne Holdings, Inc., St. Paul, MN (US)

(72) Inventor: Preston James Huddleston, Maplewood, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 148 days.

(21) Appl. No.: 17/332,424

(22) Filed: May 27, 2021

(65) Prior Publication Data
US 2021/0369257 A1 Dec. 2, 2021

Related U.S. Application Data

(60) Provisional application No. 63/031,618, filed on May 29, 2020.

(51) Int. Cl.
*A61F 2/24* (2006.01)
*A61B 17/00* (2006.01)
(Continued)

(52) U.S. Cl.
CPC .... *A61B 17/00234* (2013.01); *A61B 17/3478* (2013.01); *A61F 2/2427* (2013.01); *A61B 2017/00247* (2013.01); *A61B 2017/00323* (2013.01); *A61B 2017/00606* (2013.01); *A61F 2220/0008* (2013.01); *A61M 25/10* (2013.01)

(58) Field of Classification Search
CPC .. A61F 2/24; A61F 2/2427; A61F 2220/0008; A61F 2/243; A61F 2/2433; A61B 17/00234; A61B 17/3478; A61B 2017/00247; A61B 2017/00323;
(Continued)

(56) References Cited

U.S. PATENT DOCUMENTS

2006/0111733 A1* 5/2006 Shriver ................... A61F 2/064
606/153
2007/0112422 A1 5/2007 Dehdashtian
(Continued)

FOREIGN PATENT DOCUMENTS

AU 2014233505 A1 9/2015
AU 2014233505 B2 9/2019

OTHER PUBLICATIONS

European Search Report issued in Appln. No. 21176456.8 dated Oct. 4, 2021 (2 pages).

*Primary Examiner* — Timothy J Neal
*Assistant Examiner* — Moira E Hayes
(74) *Attorney, Agent, or Firm* — SLEMAN & LUND LLP

(57) ABSTRACT

A delivery catheter system includes a guide catheter, an anchor catheter, a collapsible and expandable anchor, a balloon formed from a portion of the positioning catheter, and a needle. The anchor may be for anchoring a prosthetic heart valve in a native heart valve. The anchor may be configured to be received within the anchor catheter. The balloon may be inflated or deflated and provide mechanical support to enable the needle to pierce a ventricle wall. A metallic guide wire can simultaneously be inserted through the aorta to outline the heart when viewed through fluoroscopic imaging.

9 Claims, 38 Drawing Sheets

(51) Int. Cl.
*A61B 17/34* (2006.01)
*A61M 25/10* (2013.01)

(58) Field of Classification Search
CPC .... A61B 2017/1135; A61B 2017/1139; A61B 2090/3966; A61M 25/10
See application file for complete search history.

(56) References Cited

U.S. PATENT DOCUMENTS

| | | |
|---|---|---|
| 2009/0048668 A1 | 2/2009 | Wilson |
| 2009/0048688 A1 | 2/2009 | Gilson et al. |
| 2014/0371846 A1* | 12/2014 | Wilson .................. A61F 2/246 623/2.11 |
| 2015/0051696 A1* | 2/2015 | Hou ................ A61M 25/0905 623/2.11 |
| 2016/0206280 A1 | 7/2016 | Vidlund et al. |
| 2017/0079790 A1 | 3/2017 | Vidlund et al. |
| 2017/0224486 A1* | 8/2017 | Delaloye ................ A61F 2/97 |
| 2017/0281343 A1 | 10/2017 | Christianson et al. |
| 2018/0049873 A1 | 2/2018 | Manash et al. |
| 2018/0200490 A1* | 7/2018 | Gianotti ............. A61M 25/104 |

\* cited by examiner

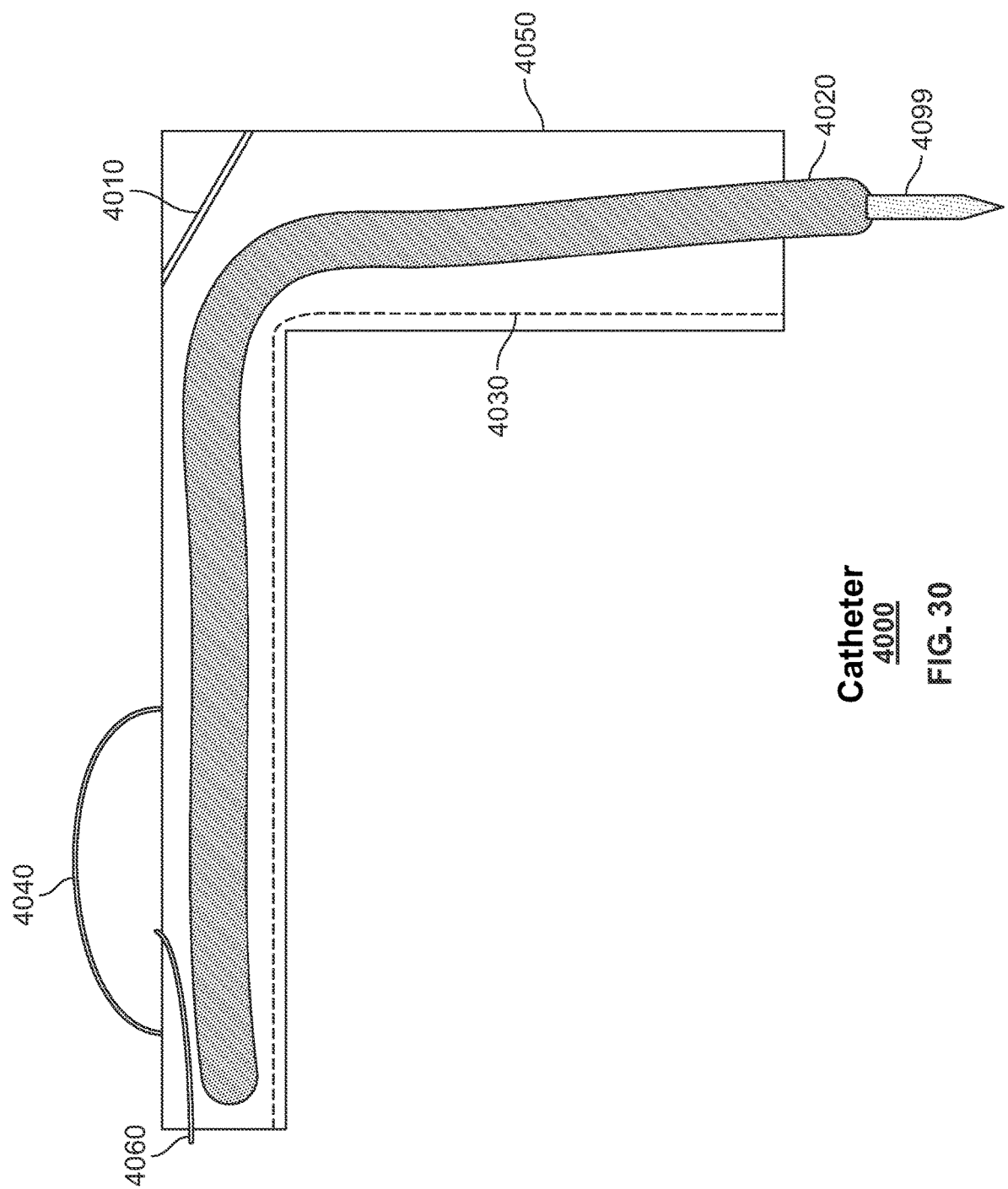

Catheter 4000

Catheter
4000

Top View of Mitral Annulus

APPARATUS AND METHODS FOR MINIMALLY INVASIVE TRANSCATHETER TRANSAPICAL PUNCTURE, IMAGING, AND CATHETER ALIGNMENT TECHNIQUES

CROSS-REFERENCE TO RELATED APPLICATIONS

The present application claims the benefit of the filing date of U.S. Provisional Patent Application No. 63/031,618 filed May 29, 2020, the disclosure of which is hereby incorporated herein by reference.

BACKGROUND OF THE DISCLOSURE

Valvular heart disease, and specifically aortic and mitral valve disease, is a significant health issue in the United States. Valve replacement is one option for treating heart valves diseases. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated with the procedure, largely due to the necessity for extra-corporeal circulation. Further, open heart surgery is often poorly tolerated in elderly patients. Thus, if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated with the native mitral valve and thus a greater level of difficulty with regard to inserting and anchoring the replacement prosthesis.

Recent developments in the field have provided devices and methods for mitral valve replacement with reduced invasion and risk to the patient. Such devices may include a prosthetic valve disposed within the native valve annulus and held in place with an anchor seated against an exterior surface of the heart near the ventricular apex, and such anchors must be at least a certain size to seat against the heart with adequate security. Methods of implanting such devices therefore typically require providing an intercostal puncture of significant size to accommodate the anchor. Trauma to the patient increases as a function of the diameter of the puncture. Accordingly, methods and devices for anchoring a prosthetic heart valve that avoid the need for an intercostal puncture, and viewing and aligning apparatuses for the same, would improve patient outcomes.

BRIEF SUMMARY OF THE DISCLOSURE

According to a first aspect of the disclosure, a delivery catheter system includes a guide catheter, an anchor catheter, a collapsible and expandable anchor for anchoring a prosthetic heart valve in a native heart valve, the anchor configured to be received within the anchor catheter, a balloon formed along a length of the guide catheter, the balloon being inflatable via a lumen in fluid communication with the balloon, and a needle positioned radially inward of the guide catheter and translatable relative to the balloon, the needle having a sharp distal tip. The balloon may be positioned a spaced distance from a distal end of the guide catheter. The needle may be solid. The needle may be hollow. The guide catheter may be steerable via at least one pull wire. The positioning catheter may be positioned radially outward of the anchor catheter and be translatable relative to the positioning catheter. The spring element positioned between the balloon and a distal end of the guide catheter, the spring element biasing the guide catheter toward a straight condition. The pull wire and the spring element may be positioned on substantially diametrically opposite sides of the guide catheter, so that pulling the pull wire tends to flex or compress the spring element. The pull wire and the balloon may be positioned on substantially opposite sides of the guide catheter, so that pulling the at least one pull wire tends to flex the distal end of the guide catheter away from the balloon.

According to another aspect of the disclosure, a method of delivering an expandable anchor for a prosthetic heart valve to a heart of a patient including advancing a guide catheter into a left atrium of the patient, the guide catheter including a balloon formed along a portion of the guide catheter, advancing an anchor catheter from within the guide catheter to a left ventricle of the heart of the patient, the anchor catheter configured to maintain the anchor in a collapsed condition, inflating the balloon so that the balloon contacts an interior wall of the left atrium, advancing a needle positioned radially within the anchor catheter distally relative to the anchor catheter and through a ventricular wall of the heart of the patient to create a transapical puncture while the balloon contacts the interior wall of the left atrium, advancing the anchor catheter at least partially through the transapical puncture, and releasing the anchor from the anchor catheter and allowing the anchor to transition from the collapsed condition to an expanded condition while the anchor catheter is positioned at least partially through the transapical puncture. The step of inflating the balloon is performed after the anchor catheter is advanced to the left ventricle. The distal end of the guide catheter may be deflected towards a native mitral valve annulus prior to advancing the anchor catheter into the left ventricle, so that the distal end of the guide catheter is substantially aligned with a central longitudinal axis passing through the native mitral valve annulus. The balloon may be formed of a compliant or semi-compliant material. The balloon may be at least partially conforms to the interior wall of the left atrium after inflating the balloon. The balloon may remain inflated against the interior wall of the left atrium after the needle is advanced through the ventricular wall and before the anchor catheter is at least partially advanced through the transapical puncture.

According to another aspect of the disclosure, a method of delivering an expandable anchor for a prosthetic heart valve to a heart of a patient may include advancing a guide wire through an aorta of the patient into a left ventricle of a patient, advancing the guide wire substantially along an interior surface of the left ventricle such that the guide wire outlines at least a portion of the left ventricle, advancing a guide catheter into a left atrium of the patient, and creating a transapical puncture in the heart by advancing a needle from the guide catheter along a trajectory through a ventricular wall of the patient. The trajectory may be determined at least partially based on an image of the guide wire under fluoroscopy. The guide catheter may be moved in a first direction substantially along a plane extending through an annulus of a native mitral valve to contact anterior and posterior leaflets of the native mitral valve to determine a first set of boundaries of the annulus. The guide catheter may be moved in a second direction substantially along the plane extending through the annulus of the native mitral valve to contact commissures of the native mitral valve to determine a second set of boundaries of the annulus. A center longitudinal axis of the annulus may be determined based on midpoints of the first and second sets of boundaries. The guide catheter may include indicia visible under fluoroscopy. The indicia on the guide catheter may include a first marker substantially aligned with a longitudinal axis of the guide catheter, and a second marker substantially aligned with a distal end of the guide catheter, the first marker being substantially perpendicular to the second marker. The first marker may be aligned with a longitudinal axis of a native mitral valve annulus prior to creating the transapical puncture in the heart. The guide catheter may include an internal catheter positioned radially within the guide catheter, the internal catheter including second indicia visible under fluoroscopy. The second indicia may include a third marker substantially aligned with a longitudinal axis of the internal catheter, and a fourth marker substantially aligned with a distal end of the internal catheter, the third marker being substantially perpendicular to the fourth marker. The internal catheter may be distally advanced relative to the guide catheter while viewing an orientation of the second indicia relative to the first indicia under fluoroscopy.

BRIEF DESCRIPTION OF THE DRAWINGS

FIG. 30 illustrates a longitudinal cross-section of a catheter with a portion that can be expanded in a balloon-like manner.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. As used herein, the terms "substantially," "generally," "approximately," and "about" are intended to mean that slight deviations from absolute are included within the scope of the term so modified.

Figure 1:
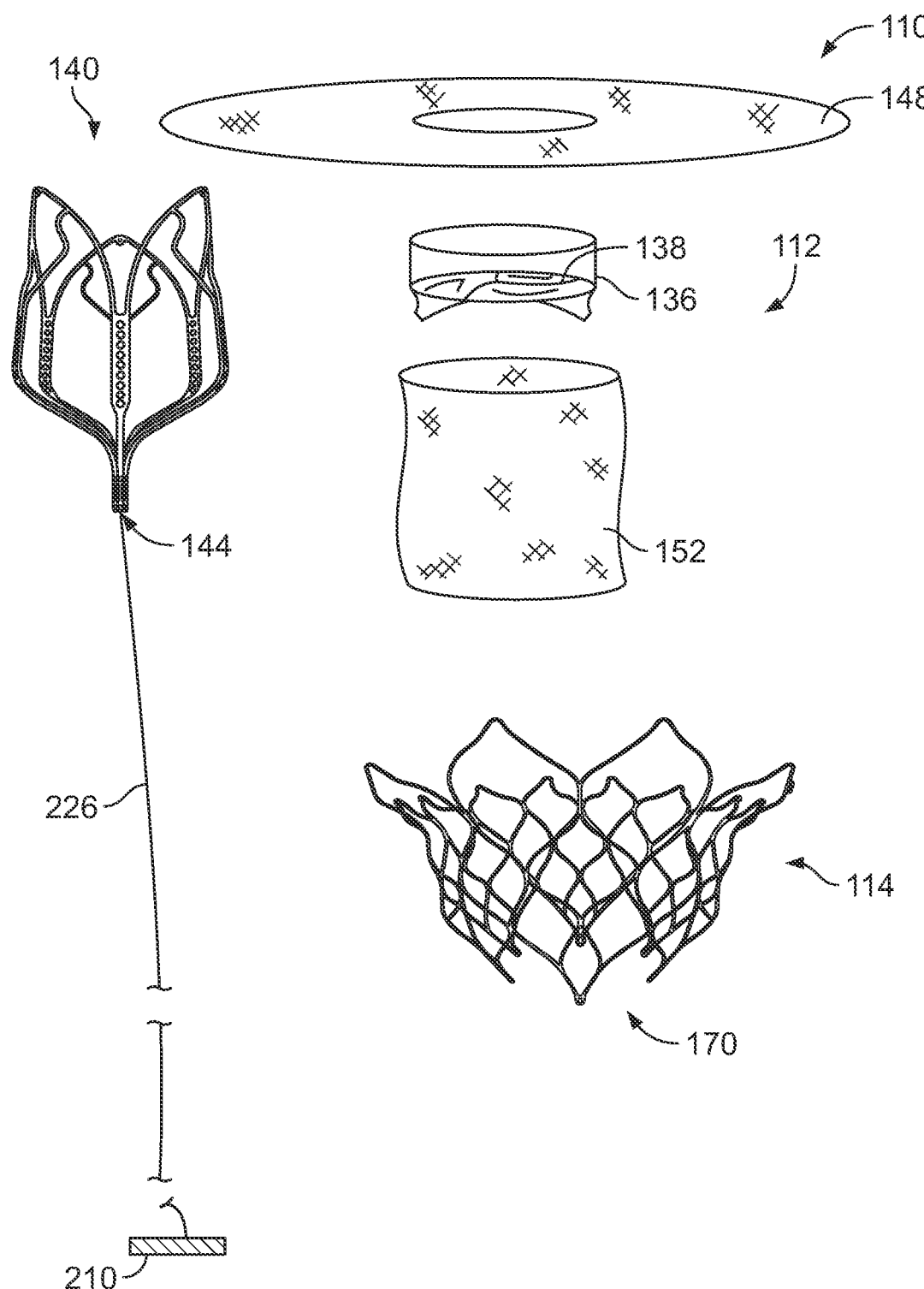
FIG. 1 is an exploded view of a prosthetic heart valve.

An exemplary prosthetic heart valve 110 as may be used with various embodiments of the present disclosure is shown in an exploded view in FIG. 1. Valve 110 includes an inner structure or assembly 112 and an outer structure or assembly 114. Valve 110 may be coupled to a tether 226 and a collapsible tether anchor 210.

Inner assembly 112 may include an inner frame 140, outer wrap 152 which may be cylindrical, and leaflet structure 136 (including articulating leaflets 138 that define a valve function). Leaflet structure 136 may be sewn to inner frame 140, and may use parts of inner frame 140 for this purpose, although method of attachment other than sutures may be suitable. Inner assembly 112 is disposed and secured within outer assembly 114, as described in more detail below.

Outer assembly 114 includes outer frame 170. Outer frame 170 may also have in various embodiments an outer frame cover of tissue or fabric (not pictured), or may be left without an outer cover to provide exposed wireframe to facilitate in-growth of tissue. Outer frame 170 may also have an articulating collar or cuff (not pictured) covered by a cover 148 of tissue or fabric.

Tether 226 is connected to valve 110 by inner frame 140. Thus, inner frame 140 includes tether connecting or clamping portion 144 by which inner frame 140, and by extension valve 110, is coupled to tether 226.

Figure 2:
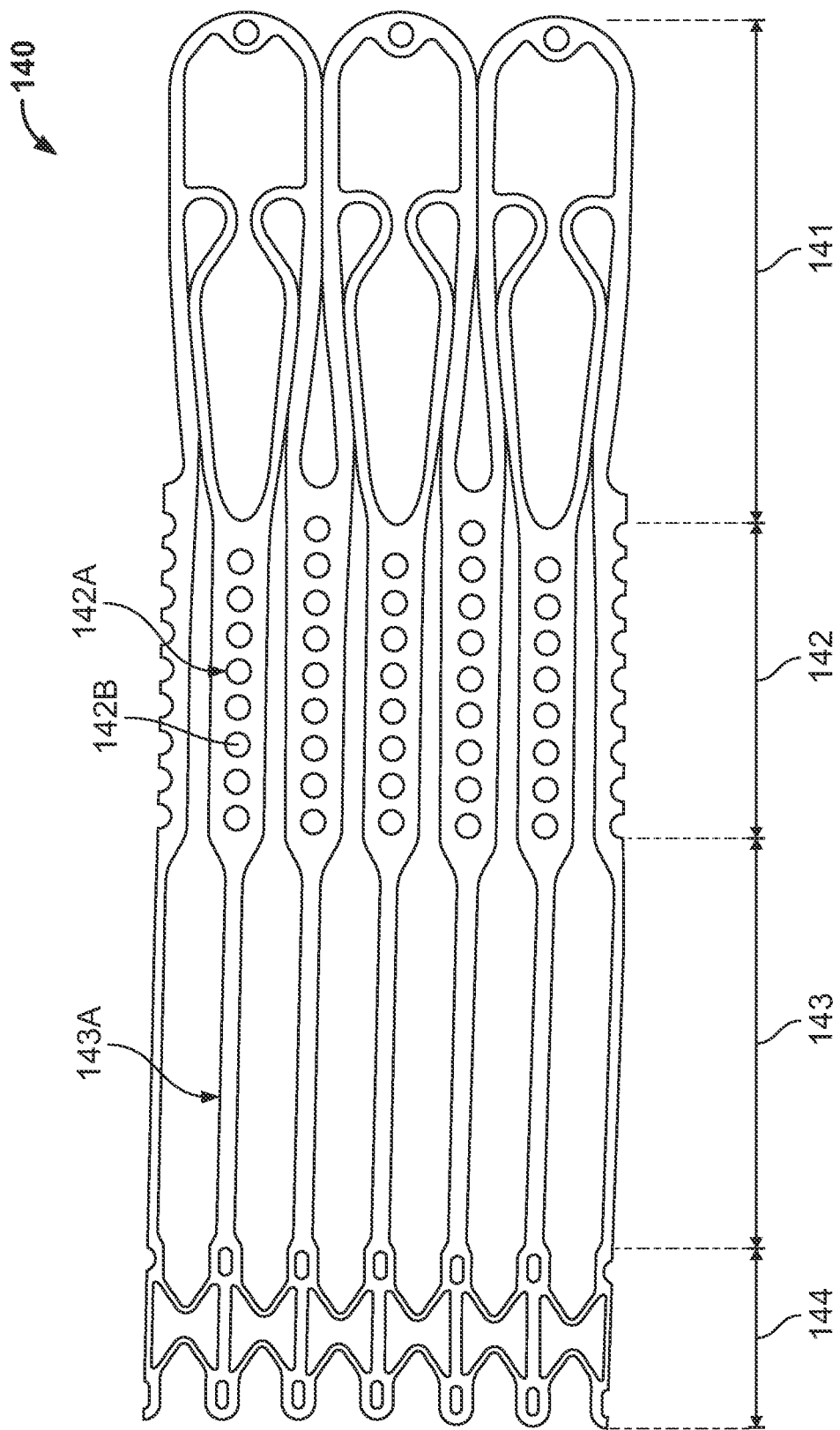
FIG. 2 is an opened and flattened view of an unexpanded inner frame of the prosthetic heart valve of FIG. 1.
Figure 3:
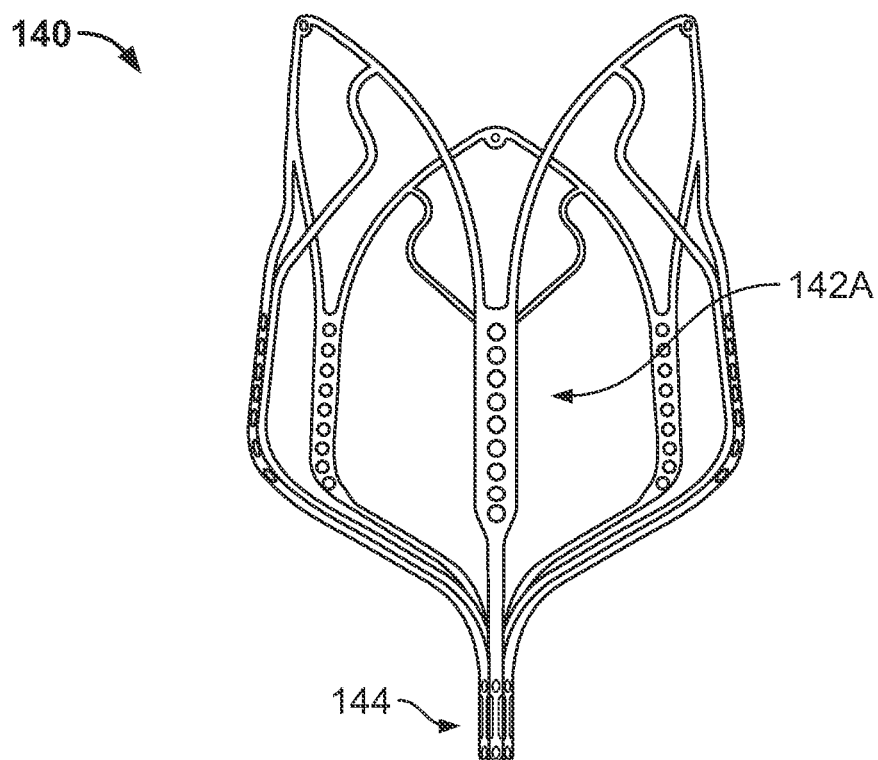
FIGS. 3 and 4 are side and bottom views, respectively, of the inner frame of FIG. 2 in an expanded configuration.
Figure 4:
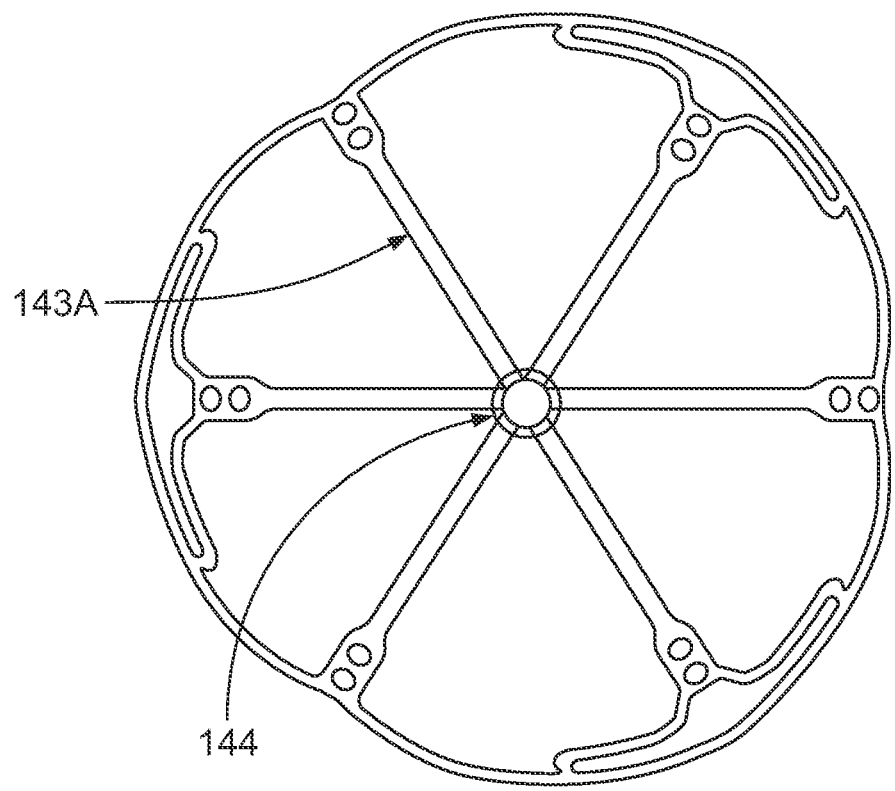

Inner frame 140 is shown in more detail in FIGS. 2-4. Inner frame 140 can be formed from a milled or laser-cut tube of a shape-memory material such as, for example, nitinol. Inner frame 140 is illustrated in FIG. 2 in an initial state, e.g., as milled or laser-cut, but cut longitudinally and unrolled into a flat sheet for ease of illustration. This initial state may generally correspond to a collapsed condition. Inner frame 140 is shown fully deformed, e.g., to the expanded, deployed configuration, in the side view and bottom view of FIGS. 3 and 4, respectively. Inner frame 140 can be divided into four portions corresponding to functionally different portions of inner frame 140 in final form: apex portion 141, body portion 142, strut portion 143, and tether connecting portion 144. Strut portion 143 includes six struts, such as strut 143A, which connect body portion 142 to connecting portion 144. A greater or lesser number of struts is contemplated herein.

Connecting portion 144 includes longitudinal extensions of the struts, connected circumferentially to one another by pairs of v-shaped connecting members, which may be referred to herein as "micro-V's." Connecting portion 144 is configured to be radially collapsed by application of a compressive force, which causes the micro-V's to become more deeply V-shaped, with each pair of vertices moving closer together longitudinally and the open ends of the V shapes moving closer together circumferentially. When collapsed, connecting portion 144 can clamp or grip one end of tether 226, either connecting directly onto a tether line (e.g., braided filament line) or onto an intermediate structure, such as a polymer or metal piece that is, in turn, firmly fixed to the tether line. The foregoing is merely exemplary and other techniques can be used to connect tether 226 to connecting portion 144.

In contrast to connecting portion 144, apex portion 141 and body portion 142 are configured to be expanded radially. Strut portion 143 forms a longitudinal connection, and radial transition, between the expanded body portion 142 and the compressed connecting portion 144.

Body portion 142 includes six longitudinal posts, such as post 142A, although the body portion may include a greater or lesser number of such posts. The posts can be used to attach leaflet structure 136 to inner frame 140, and/or can be used to attach inner assembly 112 to outer assembly 114, such as by connecting inner frame 140 to outer frame 170. In the illustrated example, posts 142A include apertures 142B through which connecting members (such as suture filaments and/or wires) can be passed to couple the posts to other structures.

Figure 5:
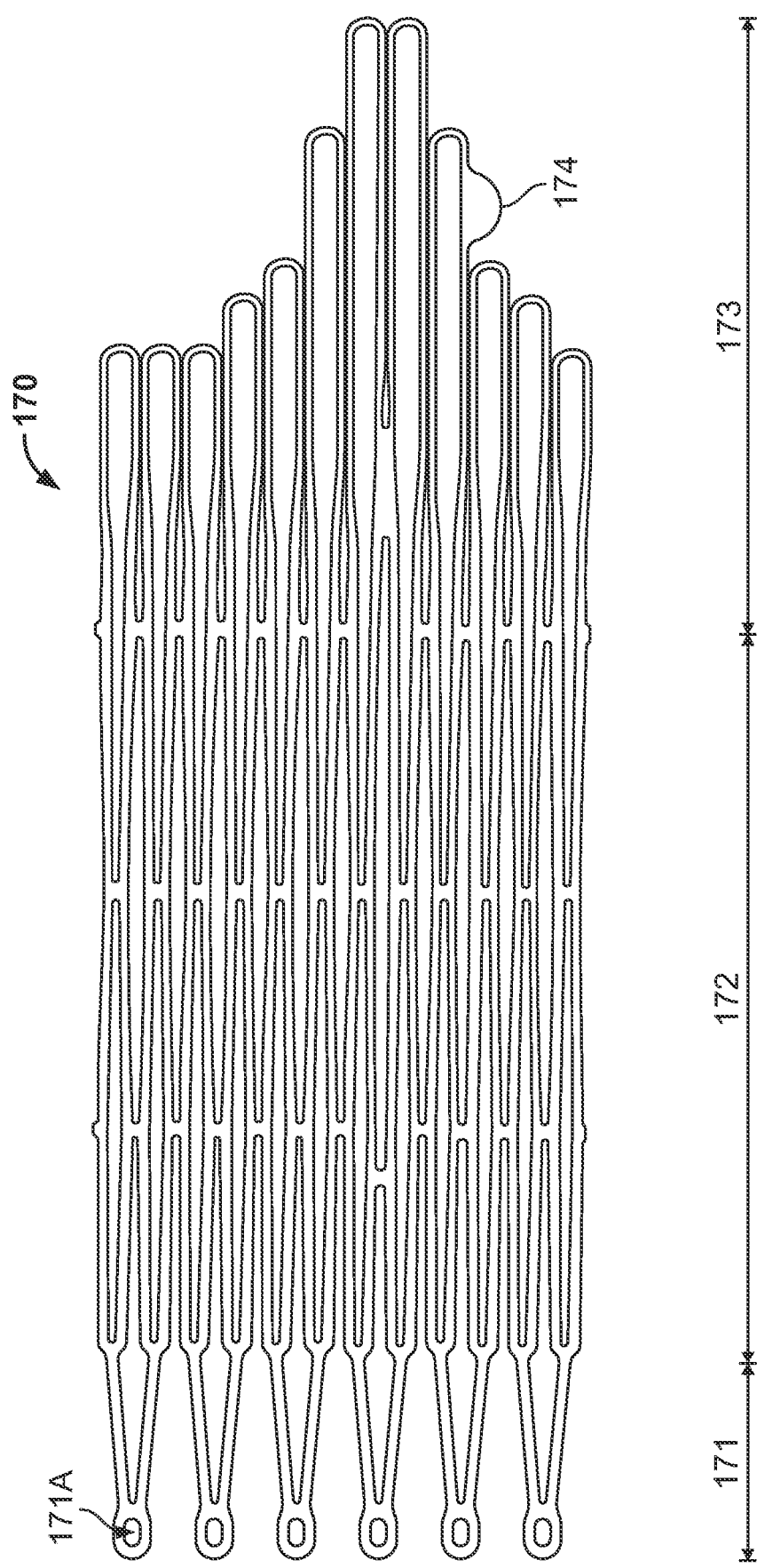
FIG. 5 is an opened and flattened view of an unexpanded outer frame of the prosthetic heart valve of FIG. 1.
Figure 6:
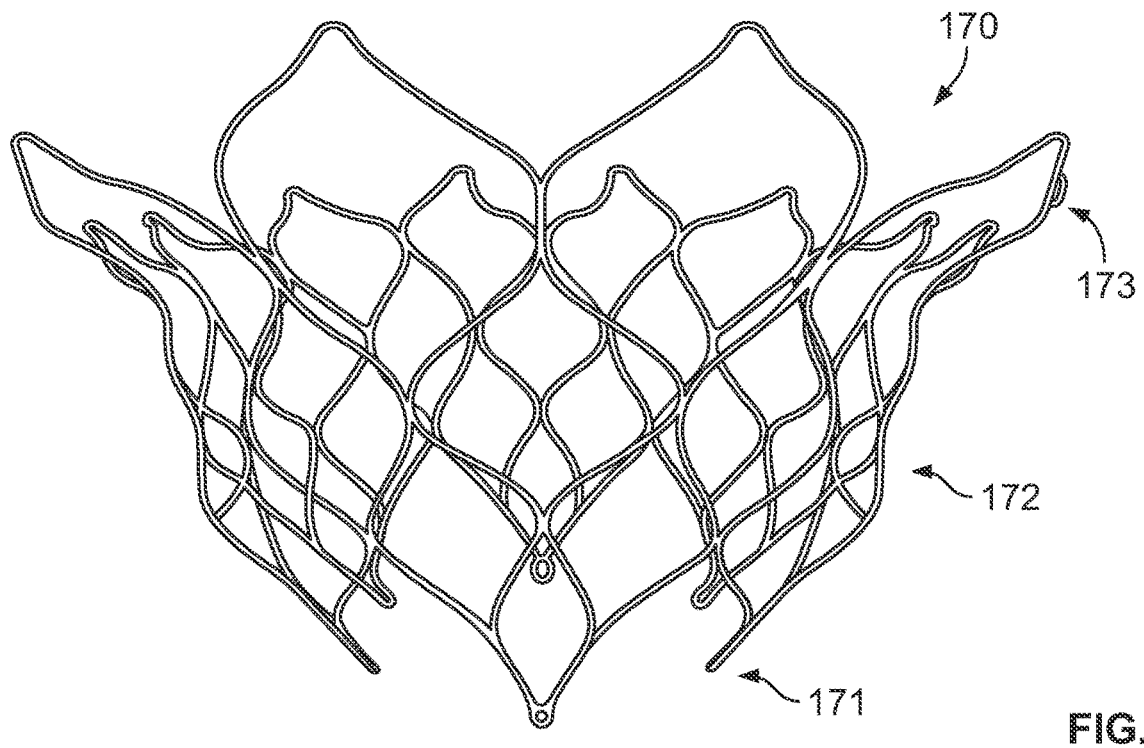
FIGS. 6 and 7 are side and top views, respectively, of the outer frame of FIG. 5 in an expanded configuration.
Figure 7:
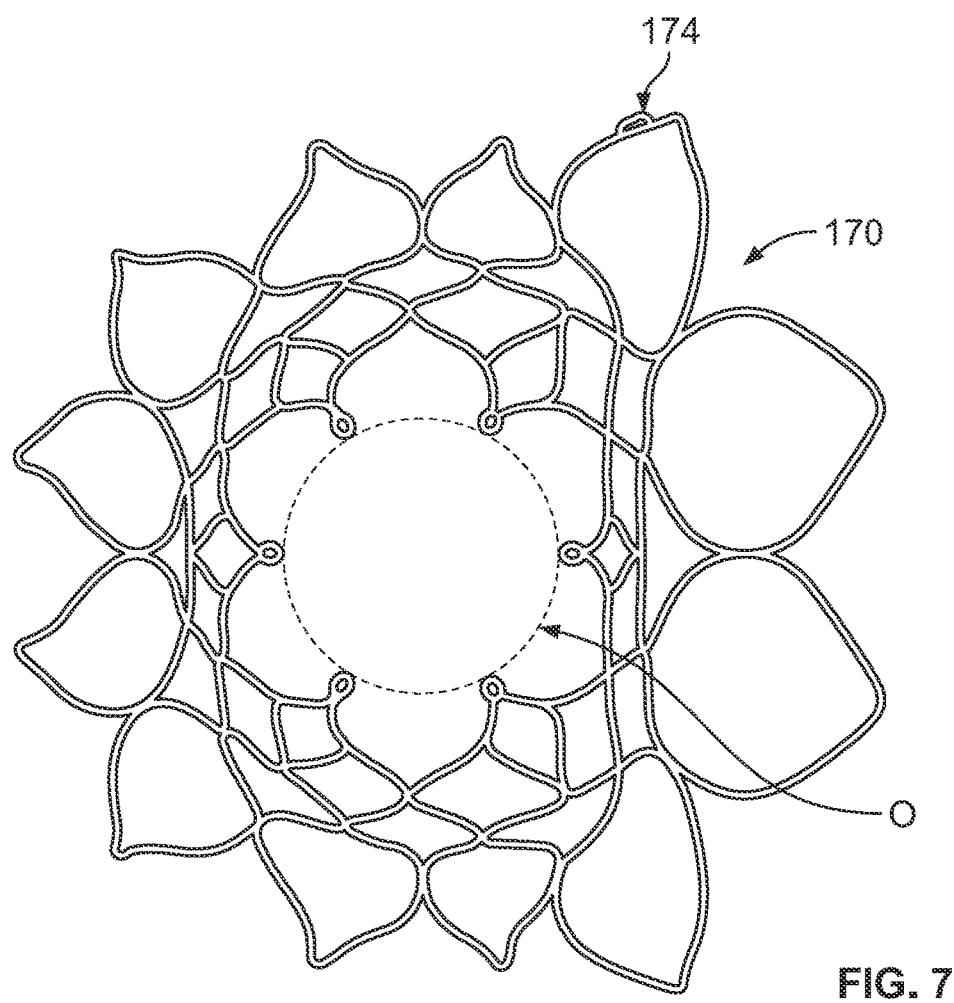

Outer frame 170 of valve 110 is shown in more detail in FIGS. 5-7. Outer frame 170 can be formed from a milled or laser-cut tube of a shape-memory material such as, for example, nitinol. Outer frame 170 is illustrated in FIG. 5 in an initial state, e.g., as milled or laser-cut, but cut longitudinally and unrolled into a flat sheet for ease of illustration. This initial state may generally correspond to the collapsed condition. Outer frame 170 can be divided into a coupling portion 171, a body portion 172, and a flared portion 173, as shown in FIG. 5. Coupling portion 171 may include multiple openings or apertures 171A by which outer frame 170 can be coupled to inner frame 140, as described in greater detail below.

Flared portion 173 may include an indicator 174. In one example, indicator 174 is simply a broader portion of the wire frame element of flared portion 173. Indicator 174 may be more apparent in radiographic or other imaging modalities than the surrounding wireframe elements of flared portion 173. In other examples, indicator 174 can be any distinguishable feature (e.g., protrusion, notch, etc.) and/or indicia (e.g., lines, markings, tic marks, etc.) that enhance the visibility of the part of flared portion 173 on which it is formed, or to which it is attached. Indicator 174 can facilitate the implantation of the prosthetic valve by providing a reference point or landmark that the operator can use to orient and/or position the valve (or any portion of the valve) with respect to the native valve annulus or other heart structure. For example, during implantation, an operator can identify (e.g., using echocardiography) indicator 174 when the valve 110 is situated in a patient's heart. The operator can therefore determine the location and/or orientation of the valve and make adjustments accordingly.

Outer frame 170 is shown in an expanded, deployed configuration, in the side view and top view of FIGS. 6 and 7, respectively. As best seen in FIG. 7, the lower end of coupling portion 171 may form a roughly circular opening (identified by "O" in FIG. 7). The diameter of this opening preferably corresponds approximately to the diameter of body portion 142 of inner frame 140, when the inner frame is in the expanded condition, to facilitate the coupling together of these two components of valve 110.

Figure 8:
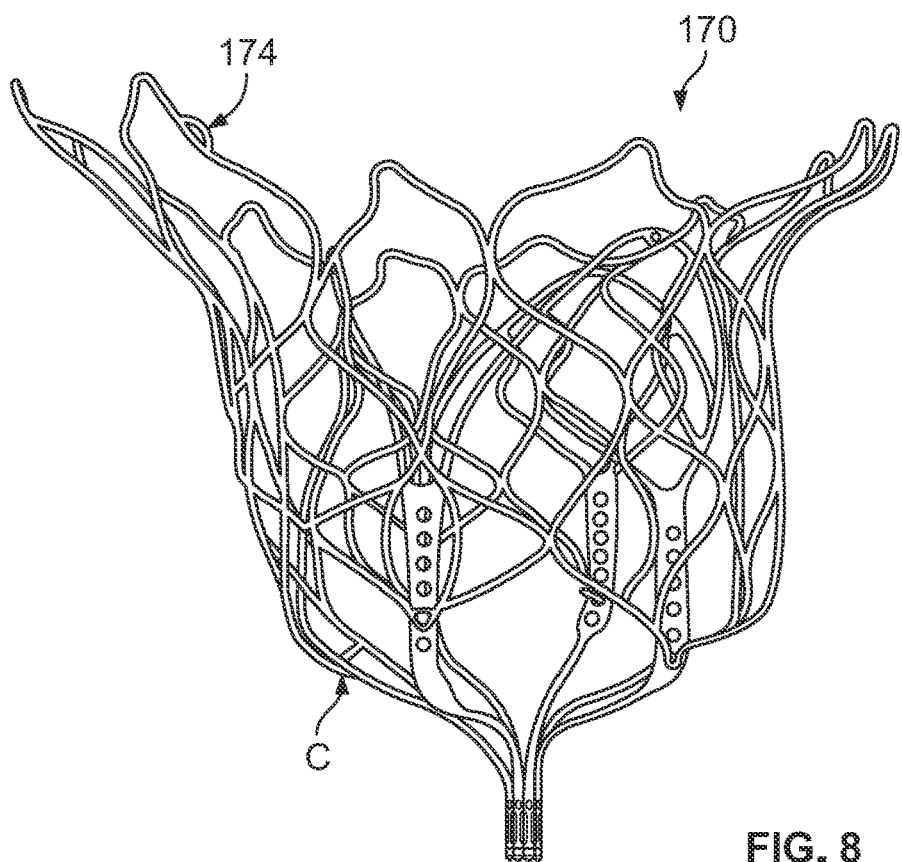
FIGS. 8-10 are side, front, and top views, respectively, of an assembly of the inner frame of FIGS. 2-4 and the outer frame of FIGS. 5-7, all in an expanded configuration.
Figure 9:
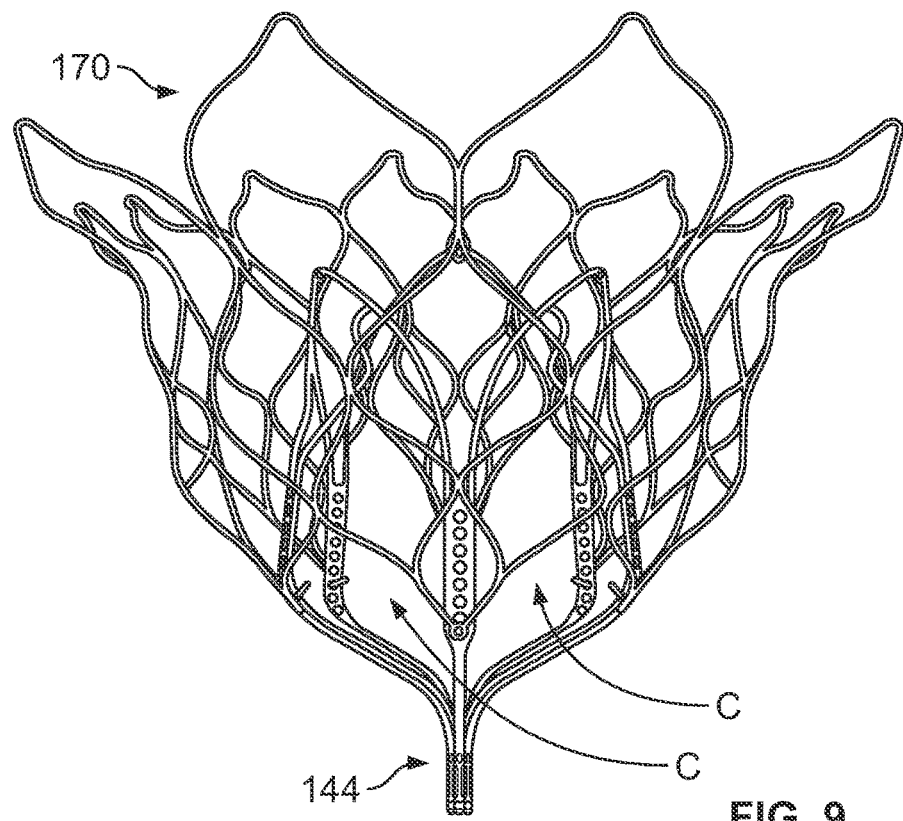
Figure 10:
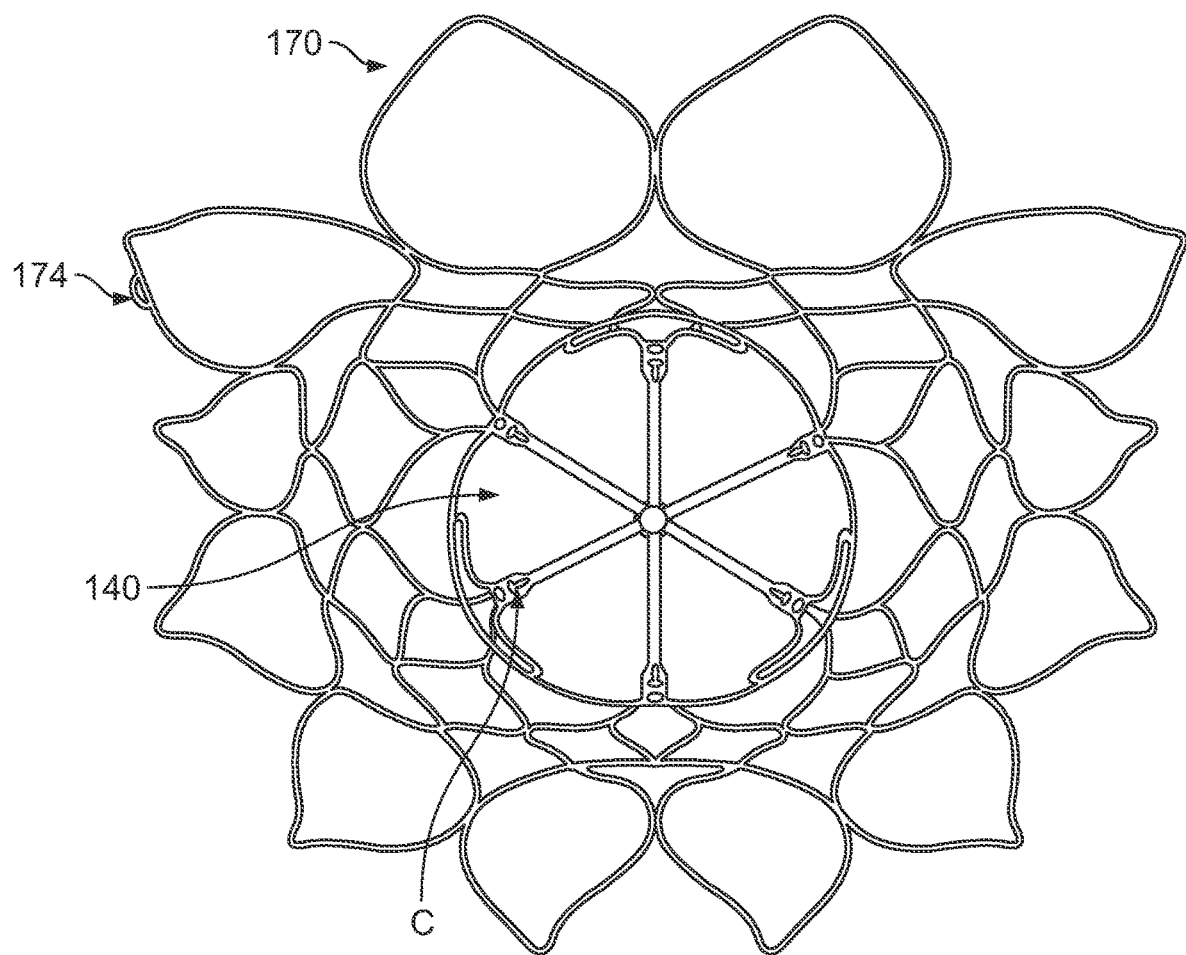

Outer frame 170 and inner frame 140 are shown coupled together in FIGS. 8-10 in front, side, and top views, respectively. The two frames collectively form a structural support for a valve leaflet structure, such as leaflet structure 136 in FIG. 1. The frames support leaflet structure 136 in the desired relationship to the native valve annulus, support the coverings for the two frames to provide a barrier to blood leakage between the atrium and ventricle, and couple to the tether 226 (by the inner frame 140) to aid in holding the prosthetic valve in place in the native valve annulus by the connection of the free end of the tether and tether anchor 210 to the ventricle wall, as described more fully below. The two frames are connected at six coupling points (representative points are identified as "C"). In this embodiment, the coupling of the frames is implemented with a mechanical fastener, such as a short length of wire, passed through an aperture 171A in coupling portion 171 of outer frame 170 and a corresponding aperture 142B in a longitudinal post 142A in body portion 142 of inner frame 140. Inner frame 140 is thus disposed within the outer frame 170 and securely coupled to it.

Figure 11A:
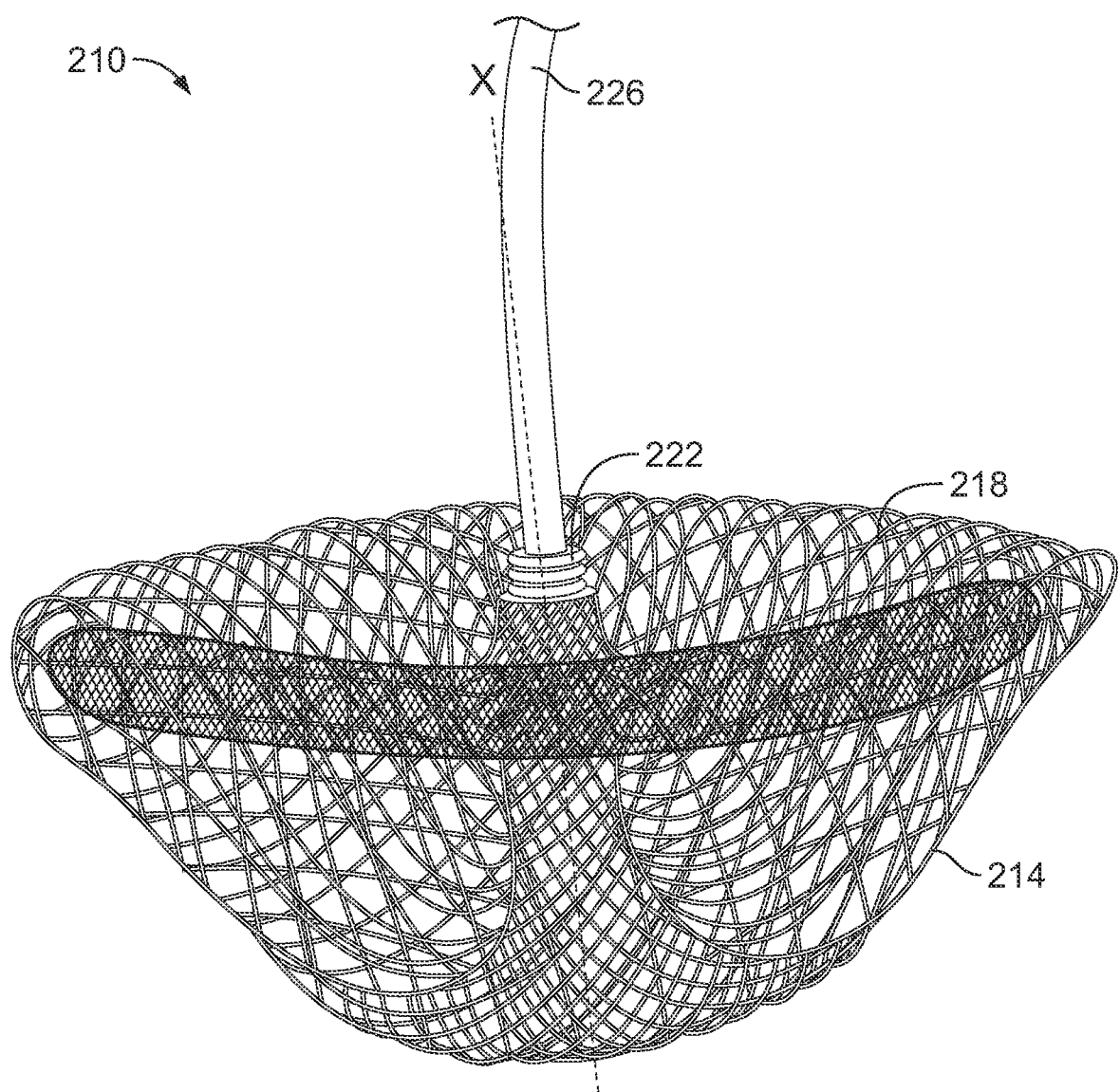
FIG. 11A is a perspective view of an anchor for the prosthetic valve of FIG. 1.
Figure 11B:
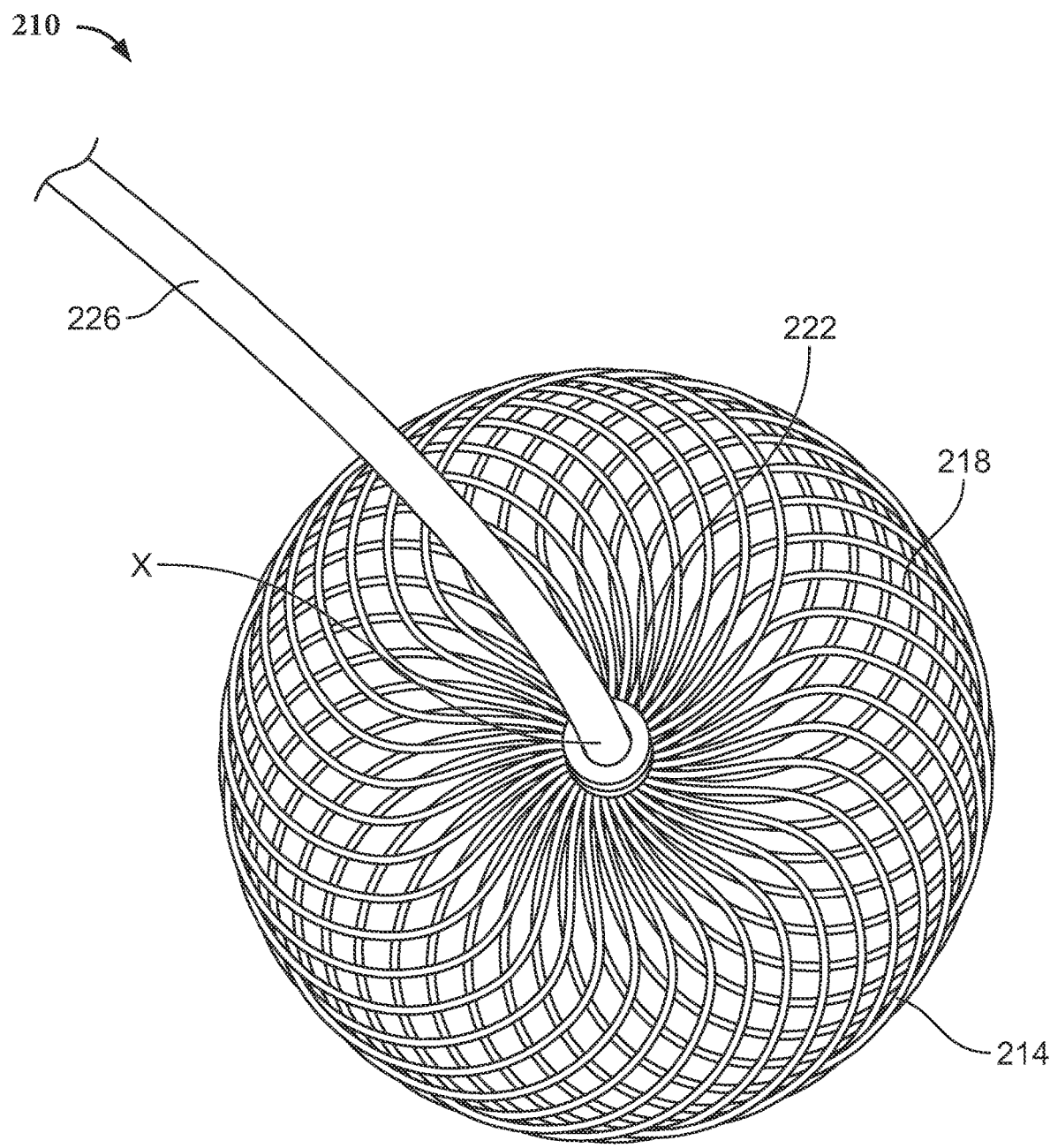
FIG. 11B is an axial view of the anchor of FIG. 11A.

An exemplary anchor 210 for a prosthetic mitral heart valve is illustrated in FIGS. 11A and 11B. Anchor 210 includes a first disc 214 and a second disc 218, both provided by a wire mesh and centered on an axis X. First disc 214 is offset from second disc 218 in a first direction along axis X. First disc 214 and second disc 218 are each biased toward a dome-shaped resting configuration that is concave toward a second direction along axis X, the second direction being opposite the first direction. The resting configuration of first disc 214 extends far enough in the second direction along axis X to partially overlap second disc 218.

Figure 12:
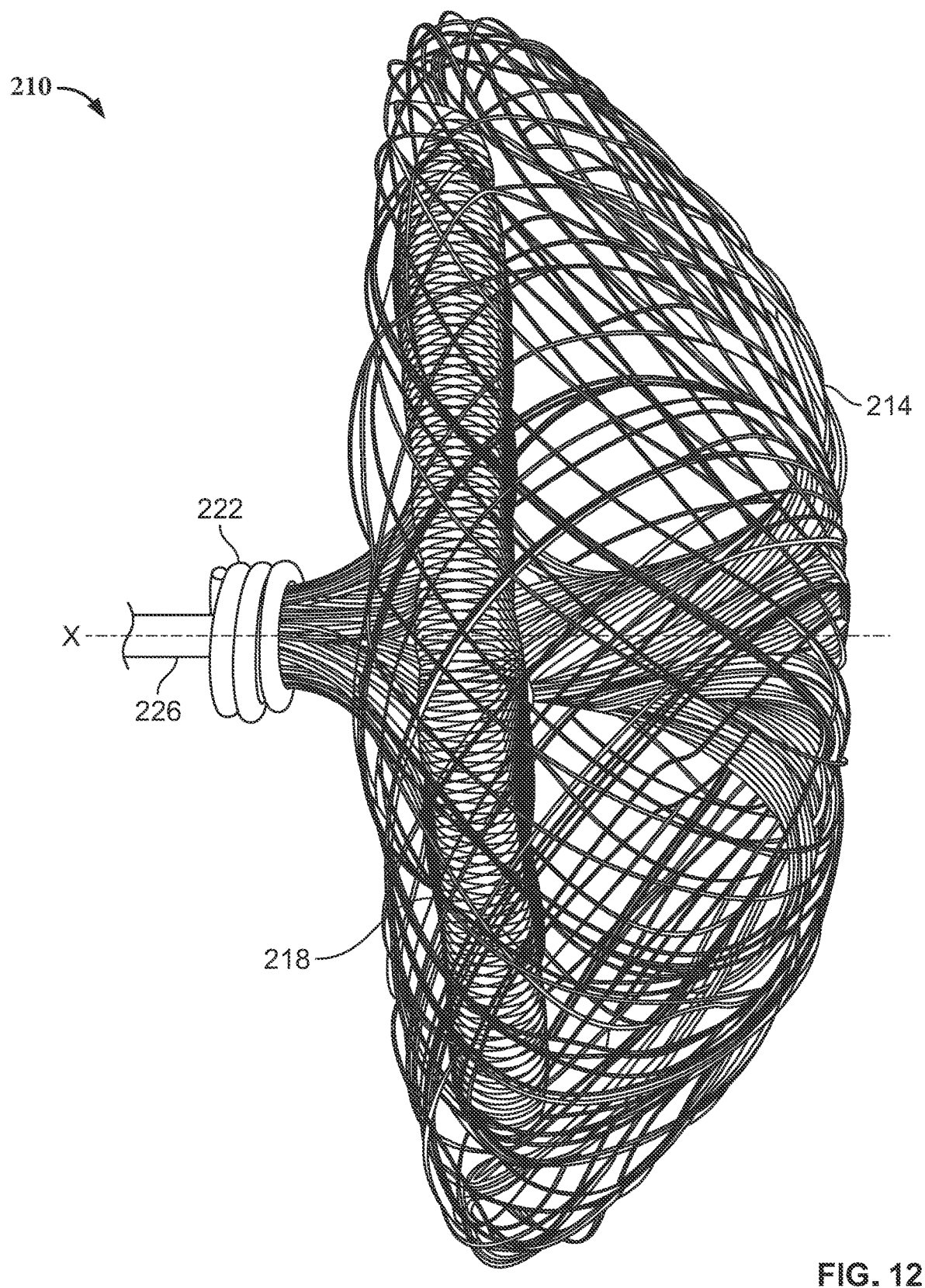
FIG. 12 is a side view of the anchor for the prosthetic valve of FIG. 1 according to another arrangement.

It should be understood that the illustrated dome shapes are merely exemplary, and first disc 214 and second disc 218 may be biased differently. For example, either or both of first disc 214 and second disc 218 may be biased toward a resting configuration that is convex toward the second direction or generally planar. Further, the first disc 214 and second disc 218 may be biased to different resting configurations. In one example, the first disc 214 may be biased toward a dome-shaped resting configuration that is concave toward the second direction while the second disc 218 is biased toward a generally planar configuration having about the same diameter location as the widest part of the dome-shaped resting configuration of the first disk 214, as shown in FIG. 12. In the arrangement shown in FIG. 12, second disc 218 is generally planar in shape with a shallow concavity toward the first direction near the center of second disc 218.

Anchor 210 may also include a cuff 222 for gripping a tether 226, which may be connected to a prosthetic heart valve. Cuff 222 is offset from second disc 218 in the second direction along axis X. One-way gripping features, such as angled teeth, within cuff 222 may permit anchor 210 to slide along tether 226 in the second direction, but not the first direction. In other embodiments, cuff 222 may be fixedly attached to tether 226 so that the anchor 210 may not slide along the tether.

Figure 13:
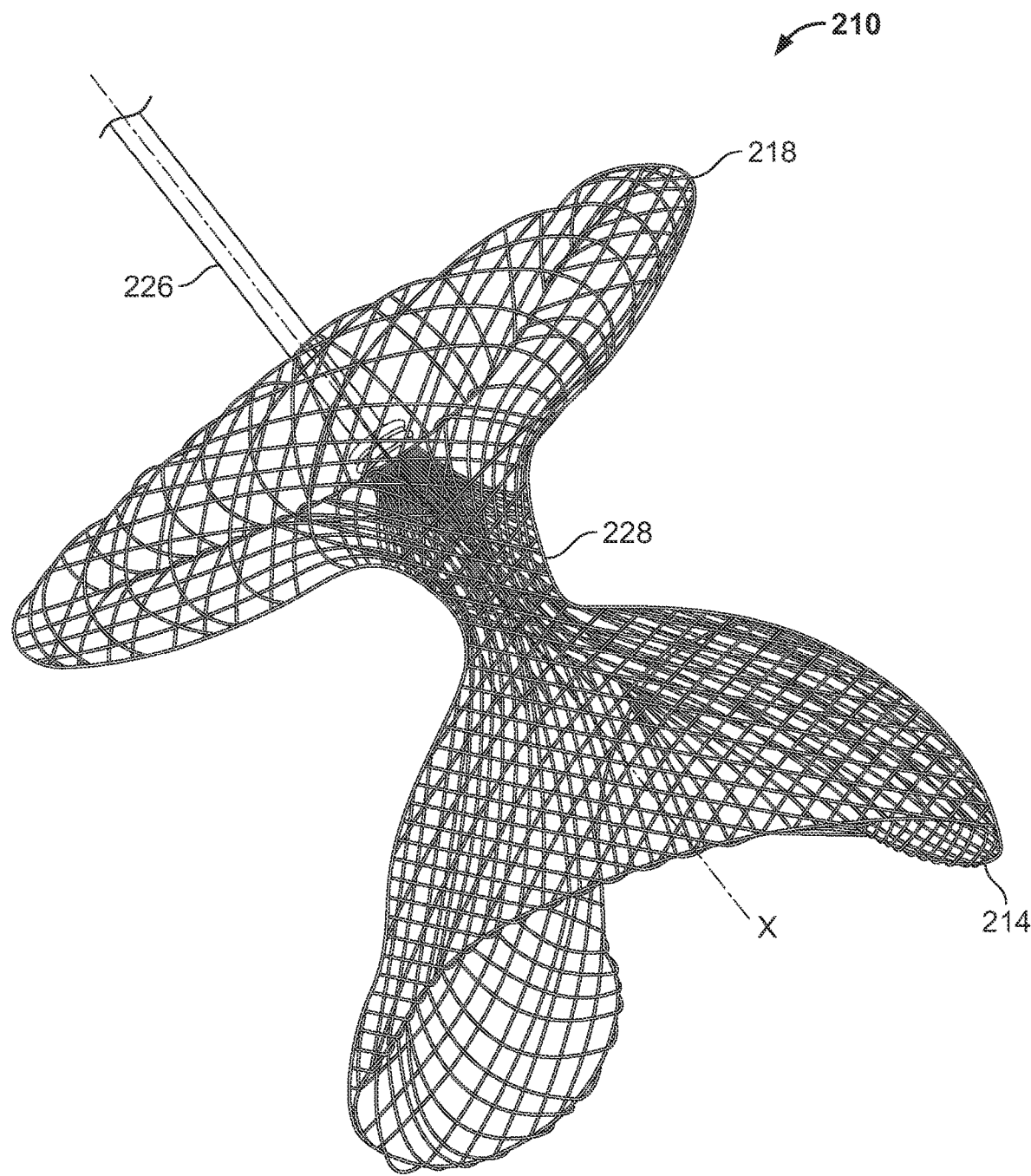
FIG. 13 is a perspective view of the anchor of FIG. 11 in a partially everted state.

Anchor 210 is flexible, as illustrated in FIG. 13, which shows anchor 210 with the first disc 214 everted from its resting configuration. First disc 214 is connected to second disc 218 by a neck 228 extending between first disc 214 and second disc 218. In the illustrated example, neck 228 is centered on axis X, but in other examples neck 228 may be radially offset from axis X. First disc 214, second disc 218, and neck 228 may all be constructed from a single continuous piece or tube of wire mesh. The wire mesh may be formed from a plurality of strands or wires braided into various three-dimensional shapes and/or geometries to engage tissues, or from one or more sheets cut to provide mesh, such as by laser. In one example, the wires form a braided metal fabric that is resilient, collapsible and capable of heat treatment to substantially set a desired shape. One class of materials which meets these qualifications is shape-memory alloys, such as nitinol. The wires may comprise various materials other than nitinol that have elastic and/or memory properties, such as spring stainless steel, tradenamed alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of anchor 210. Shape memory materials such as nitinol may be particularly suitable for anchor 210 in that shape memory material construction enables anchor 210 to consistently return to an intended shape after being compressed and deployed. In other arrangements, anchor 210 may be covered by or may incorporate other flexible biocompatible material, such as a fabric.

Figure 14:
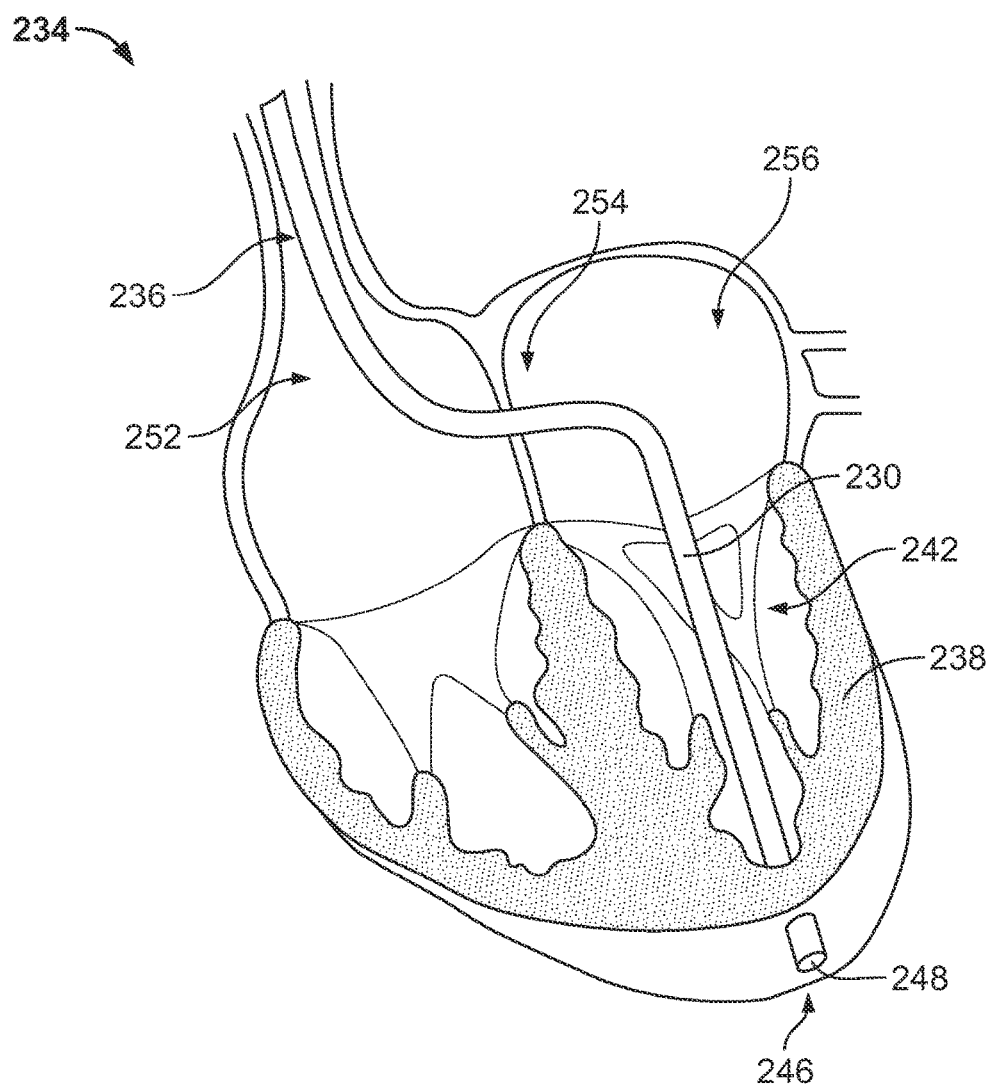
FIG. 14 illustrates a trans-jugular insertion of a delivery tube for the anchor of FIG. 11.

FIG. 14 shows a trans-jugular insertion of an at least partially flexible delivery tube 230 for anchor 210 and valve 110. Delivery tube 230 may be formed of any known material for building catheters, including biocompatible metals such as steel, and may be part of a steerable or flexible catheter system. Delivery tube 230 may include an inflexible portion near its distal end to facilitate the intended puncture of tissue and guidance of valve 110. Delivery tube 230 is inserted through the patient's jugular vein (not shown), then through superior vena cava 236, right atrium 252, atrial septum 254, left atrium 256, native mitral valve 260, and into left ventricle 242. Tube 230 exits left ventricle 242 through ventricular wall 238 at or near the apex 246 of heart 234. A retractable puncturing device (not shown) and a retractable atraumatic tip (not shown) may extend from the distal open end 248 of tube 230 in alternate stages of insertion of tube 230. The puncturing device may produce openings through atrial septum 254 and ventricular wall 238 while the atraumatic tip may act to prevent injury to other tissue. Once delivery tube 230 has been fully inserted, the distal open end 248 of tube 230 is positioned outside of ventricular wall 238. The trans-jugular insertion of tube 230 may be accomplished by any of variety of methods, such as, for example, guiding tube 230 along a guide wire, such as a shape-memory guide wire, inserted through the jugular vein. The flexible nature of anchor 210 allows trans-jugular delivery of anchor 210 through tube 230. Because tube 230, anchor 210, and valve 110 all reach heart 234 from the jugular vein, valve 110 and anchor 210 may be delivered and implanted without any intercostal puncture.

Figure 15:
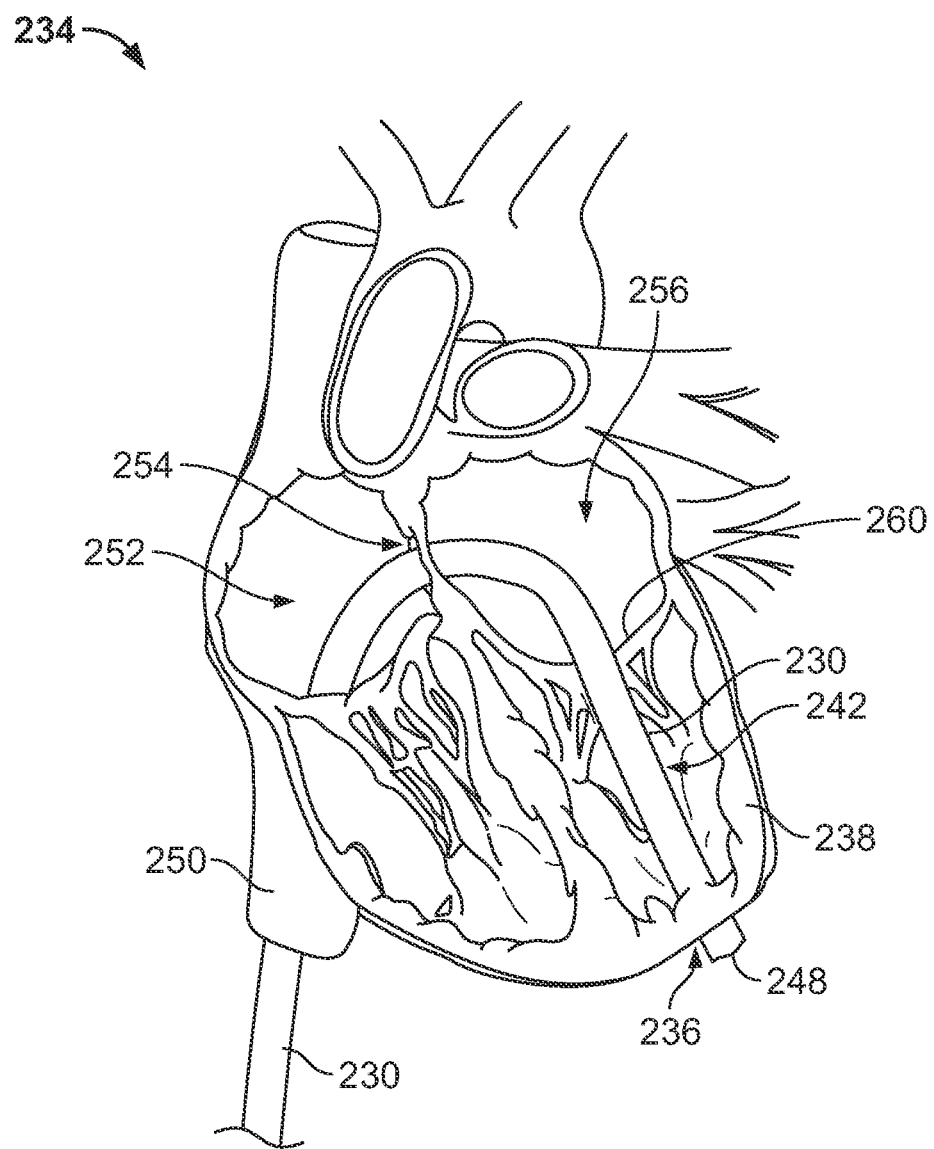
FIG. 15 illustrates a trans-femoral insertion of the delivery tube of FIG. 14.
Figure 16:
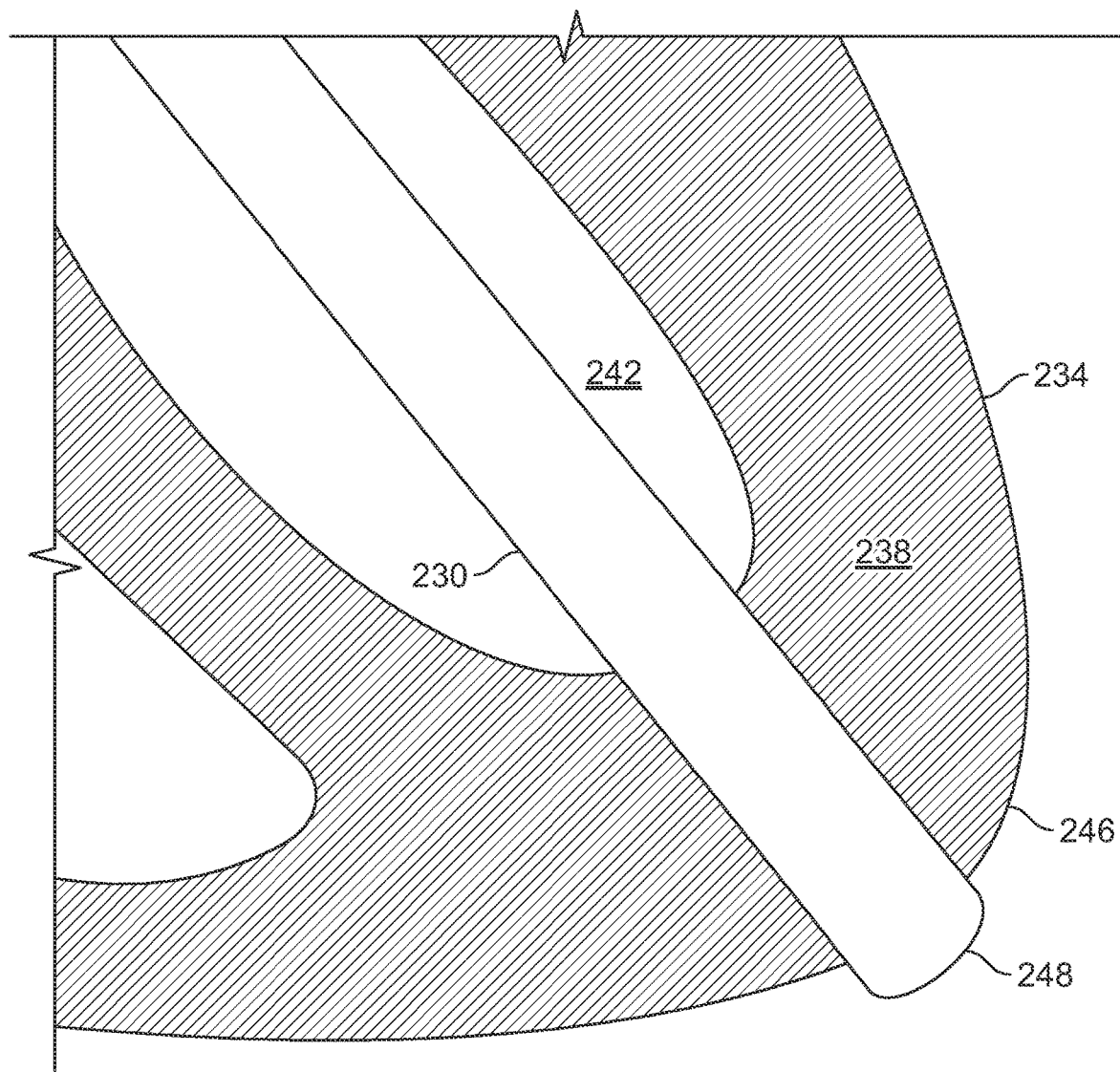
FIG. 16 illustrates the delivery tube of FIGS. 14 and 15 extending through a wall of a heart.

FIG. 15 shows a trans-femoral insertion of tube 230. Tube 230 enters heart 234 through inferior vena cava 250, travels through right atrium 252, and punctures septum 254 to enter left atrium 256. Tube 230 is advanced from left atrium 256 through native mitral valve 260, left ventricle 242, and ventricular wall 238 such that the open end 248 of the tube is positioned outside of wall 238 at or near apex 246. As with trans-jugular insertion, guidance of tube 230 during trans-femoral insertion may be accomplished using a variety of methods, including guidance along a guide wire.

The trans-jugular and trans-femoral insertions described above are merely exemplary. It should be understood that tube 230 could be guided toward heart 234 using any suitable method known in the art.

Figure 17:
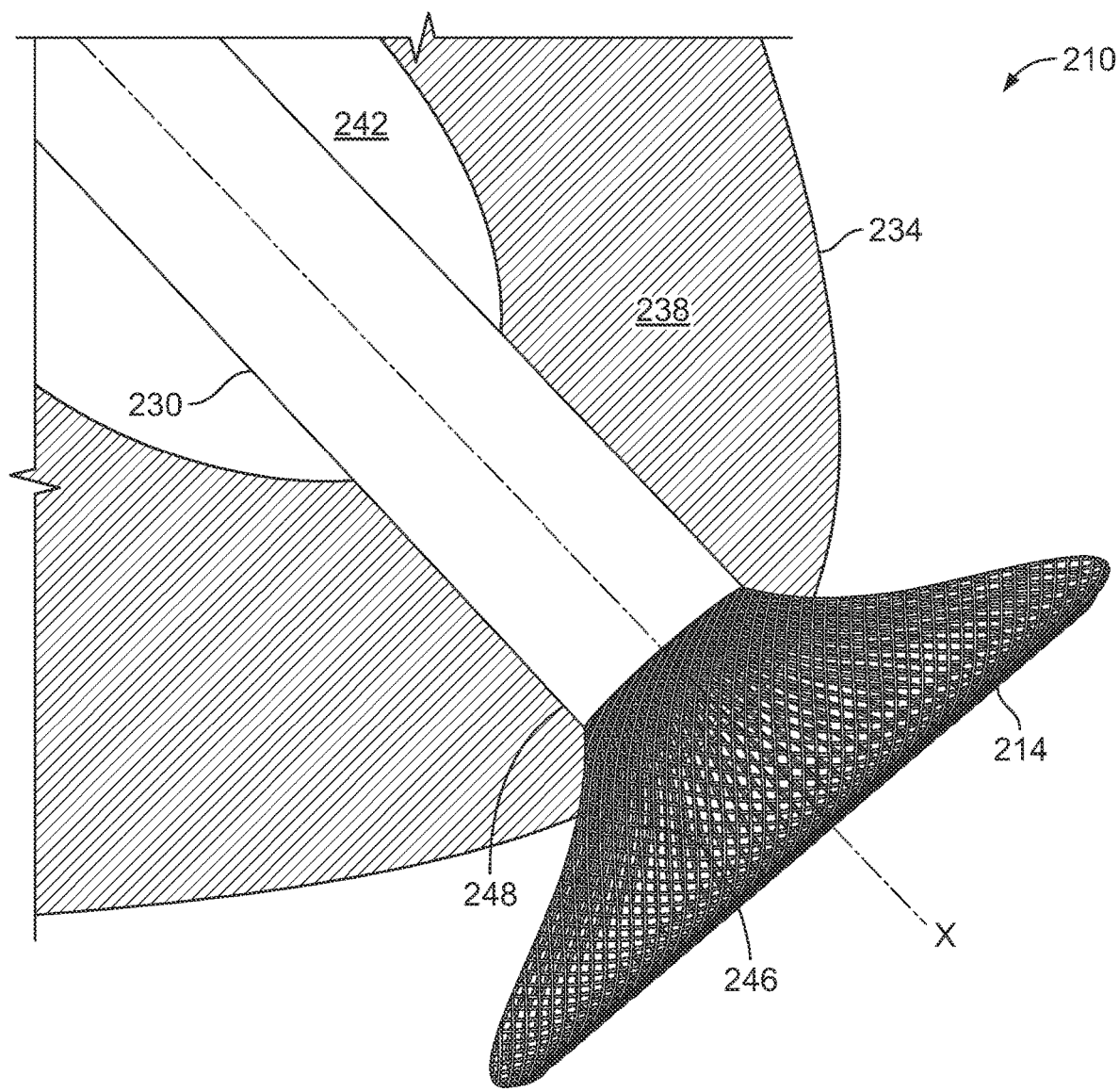
FIGS. 17-20 illustrate the anchor of FIG. 11 in progressive stages of deployment from the delivery tube of FIGS. 14 and 15.
Figure 18:
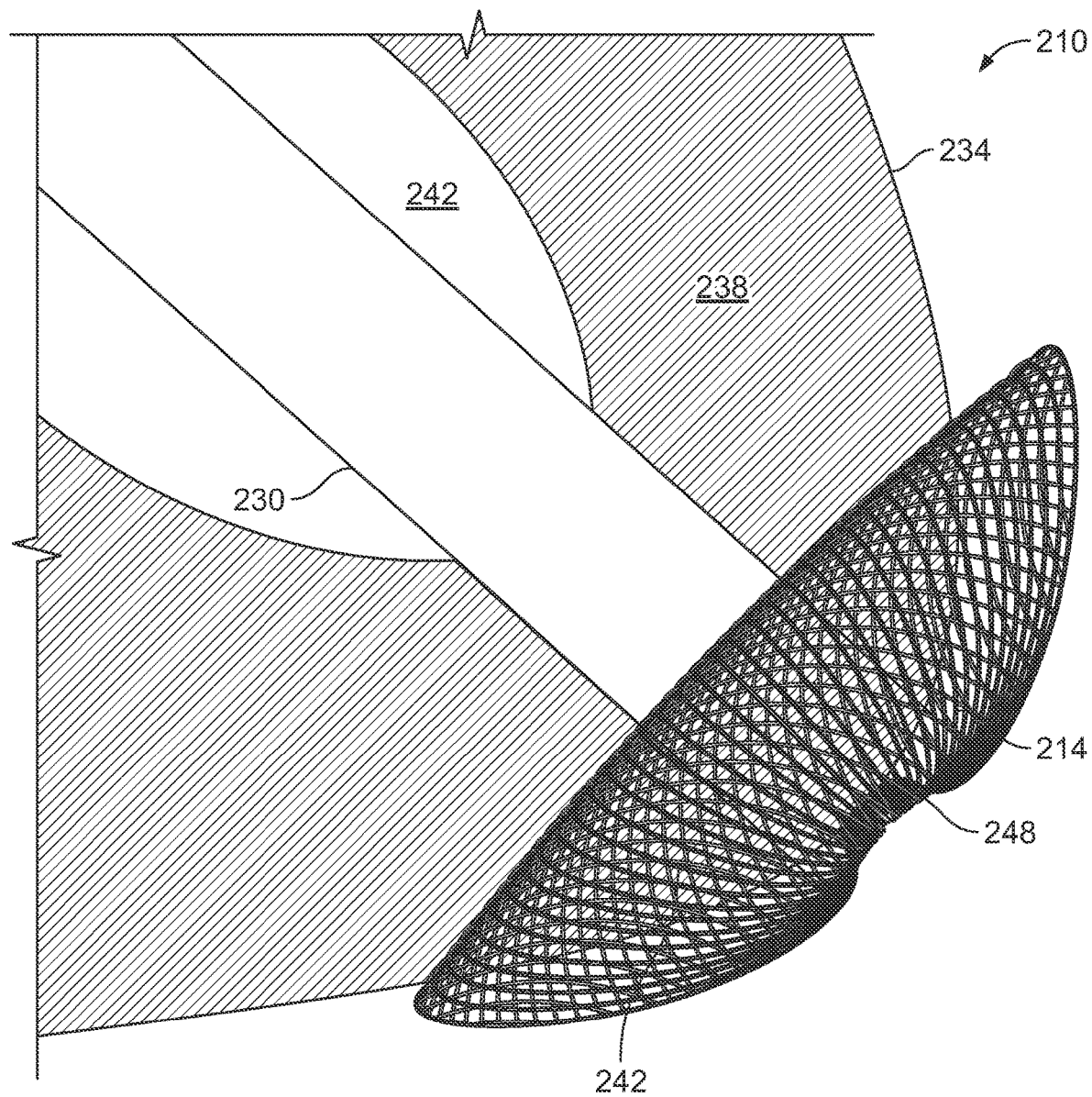
Figure 19:
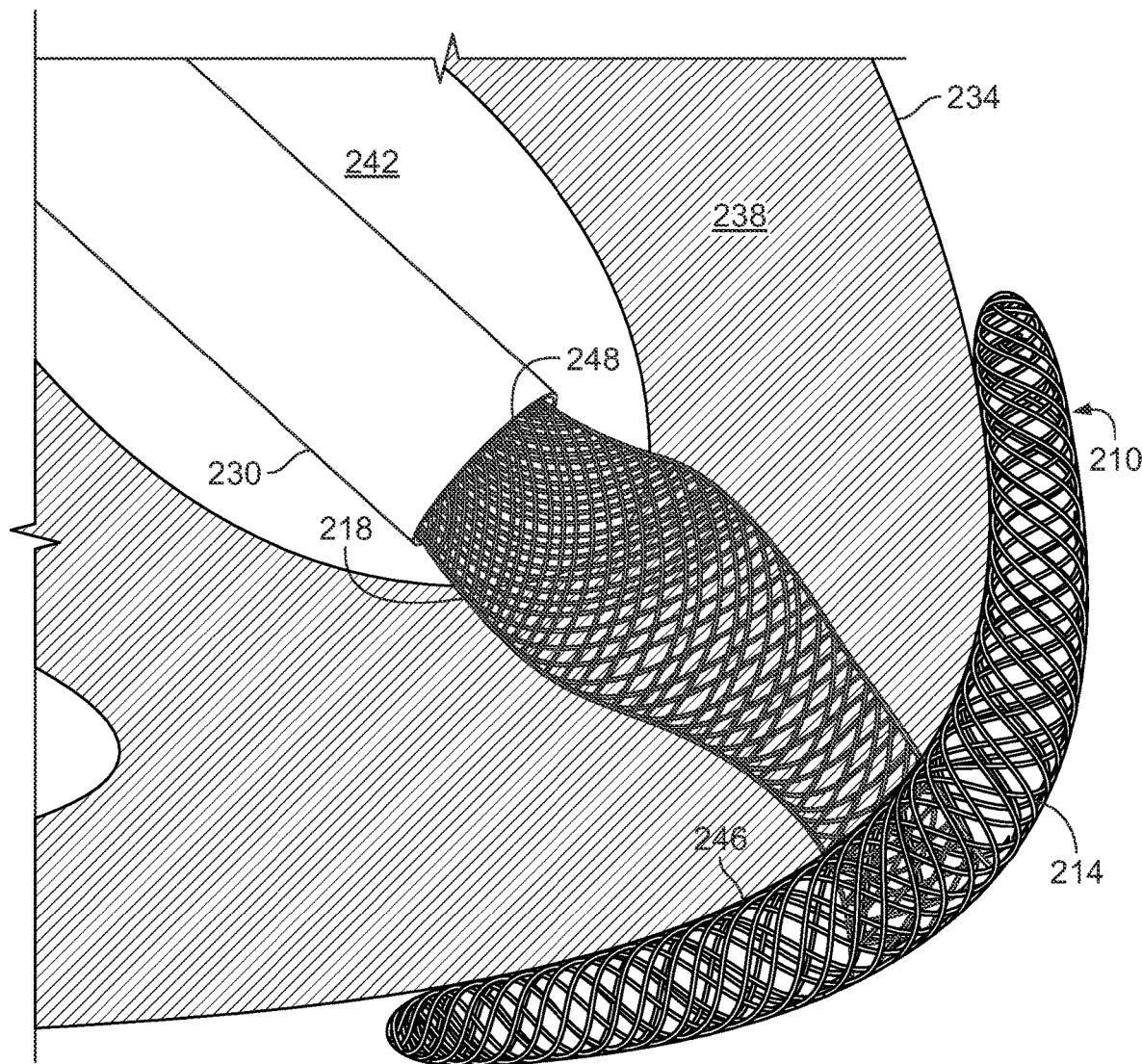
Figure 20:
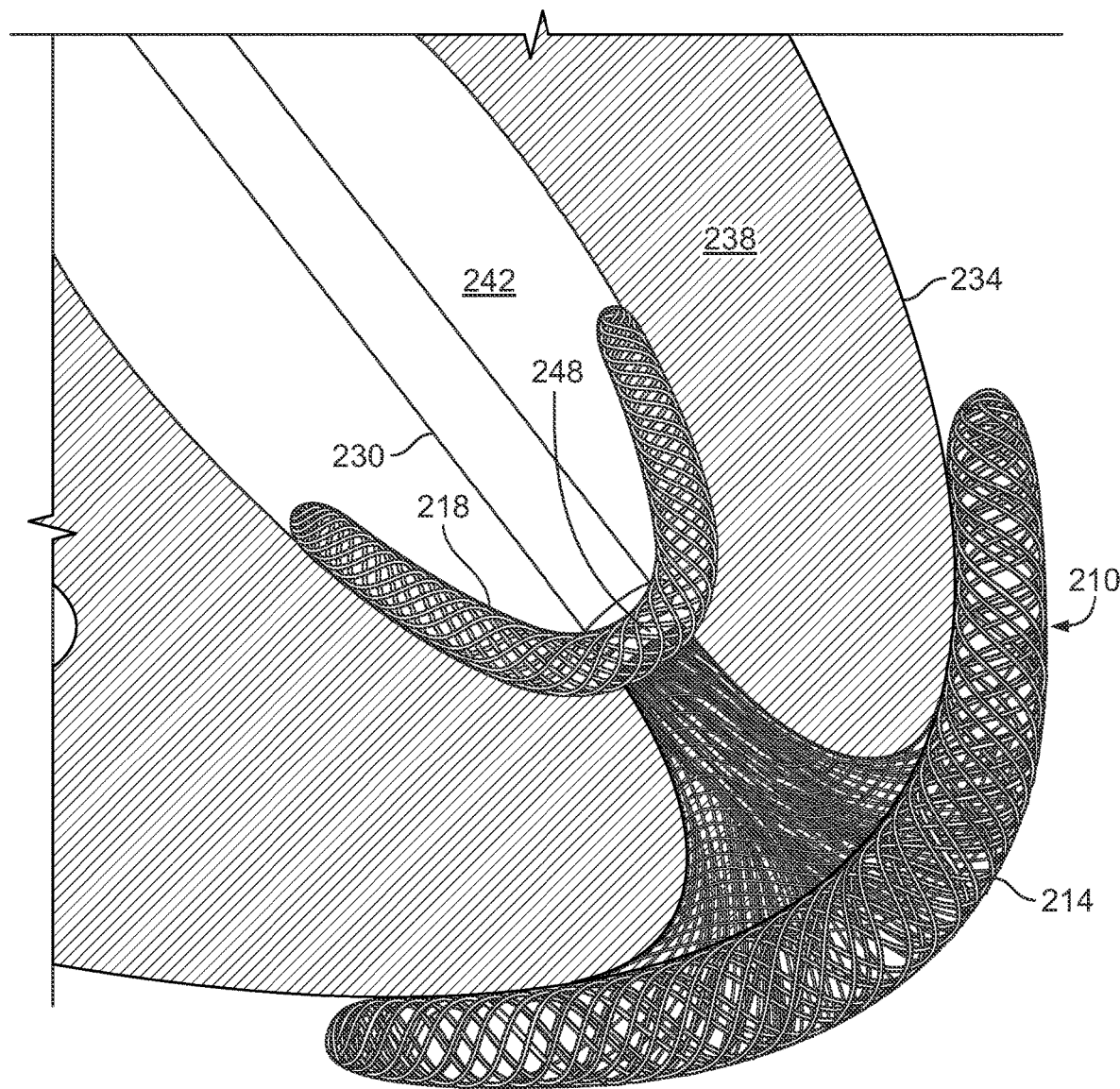
Figure 21A:
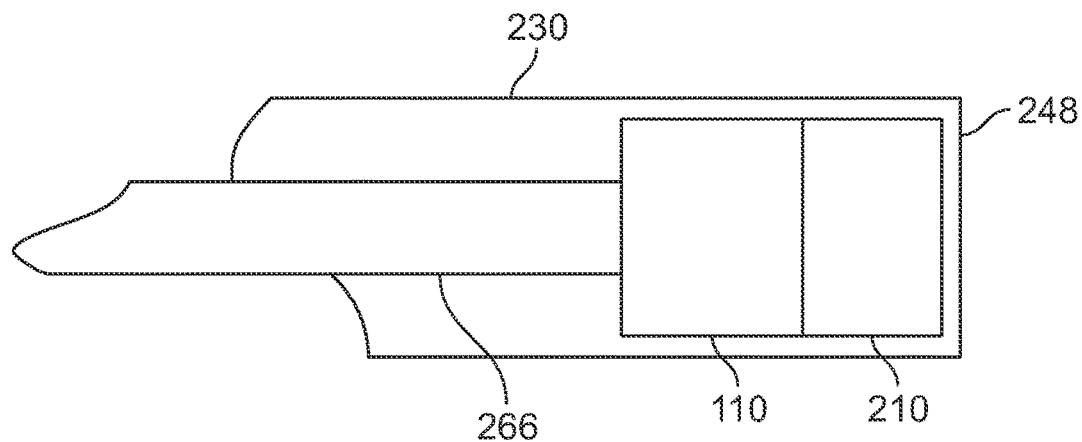
FIGS. 21A and 21B illustrate the delivery tube being retracted from the prosthetic valve of FIG. 1 and the anchor of FIG. 11.
Figure 21B:
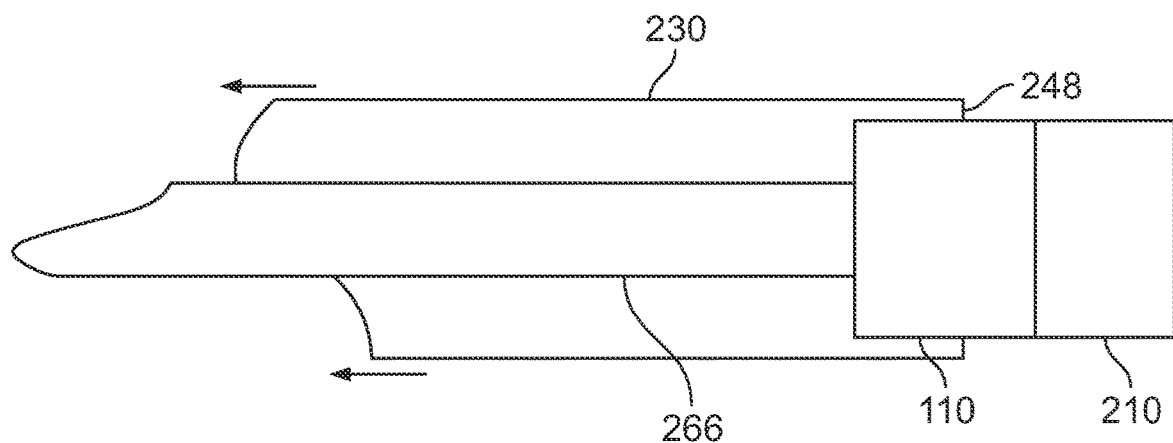

FIGS. 16-20 illustrate anchor 210 in progressive stages of deployment from the open end 248 of tube 230. Tube 230 is shown in a distalmost position in FIG. 16, with open end 248 positioned outside of heart 238. Tube 230 may be retracted while anchor 210 is forced to remain in place, such as by a reversal of a typical Bowden cable arrangement. For example, a semi-rigid cable or wire 266 may be inserted through tube 230 to contact the proximal end of valve 110, as shown in FIG. 21A. Pulling tube 230 proximally relative to wire 266 causes valve 110 and anchor 210 to deploy out from the open end 248 of tube 230, as shown in 21B. As shown in FIG. 17, retracting tube 230 while preventing anchor 210 from retreating with the tube into heart 234 causes first disc 214 of anchor 210 to deploy out from the open end 248 of tube 230 and expand radially relative to axis X. Upon further retraction of tube 230, the bias of first disc 214 causes it to curve back onto the outer apex 246 of heart 234, as shown in FIG. 18. Further retraction of tube 230 in FIG. 19 allows second disc 218 to deploy and expand radially relative to axis X within left ventricle 242 until second disc 218 opens to press against an inner side of wall 238, as shown in FIG. 20. Pressure against wall 238 results from the elastic bias of first disc 214 and second disc 218 toward certain resting positions as described above with regard to FIGS. 11A, 11B, and 12. First disc 214 and second disc 218 pressing on opposite sides of wall 238 causes anchor 210 to grip wall 238. Such progressive expansion from within a narrow tube results in anchor 210 adequately securing valve 110 to ventricular wall 238 without requiring an intercostal puncture through the patient's chest.

Figure 22:
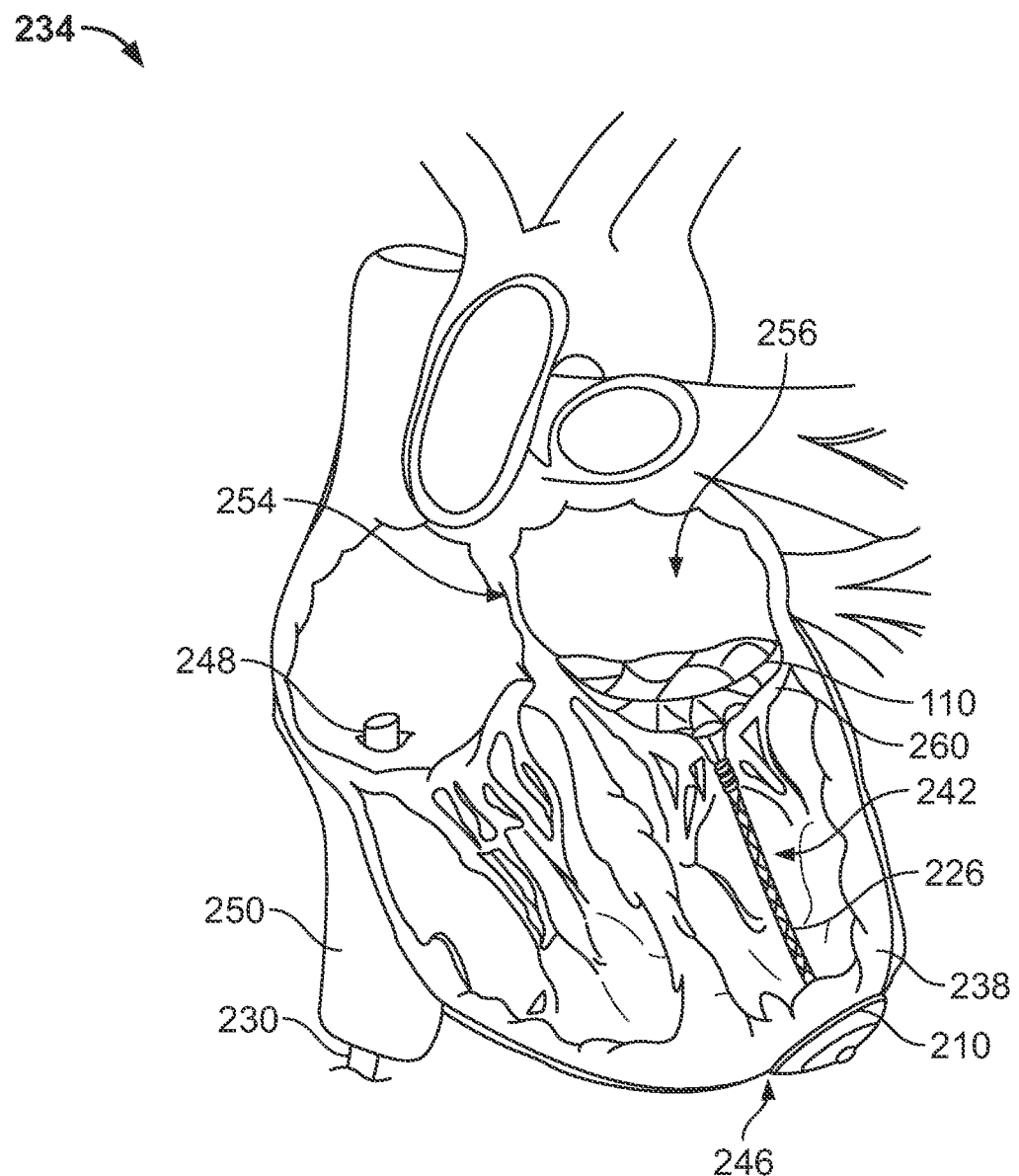
FIG. 22 illustrates the valve of FIG. 1 implanted in a heart.
Figure 23:
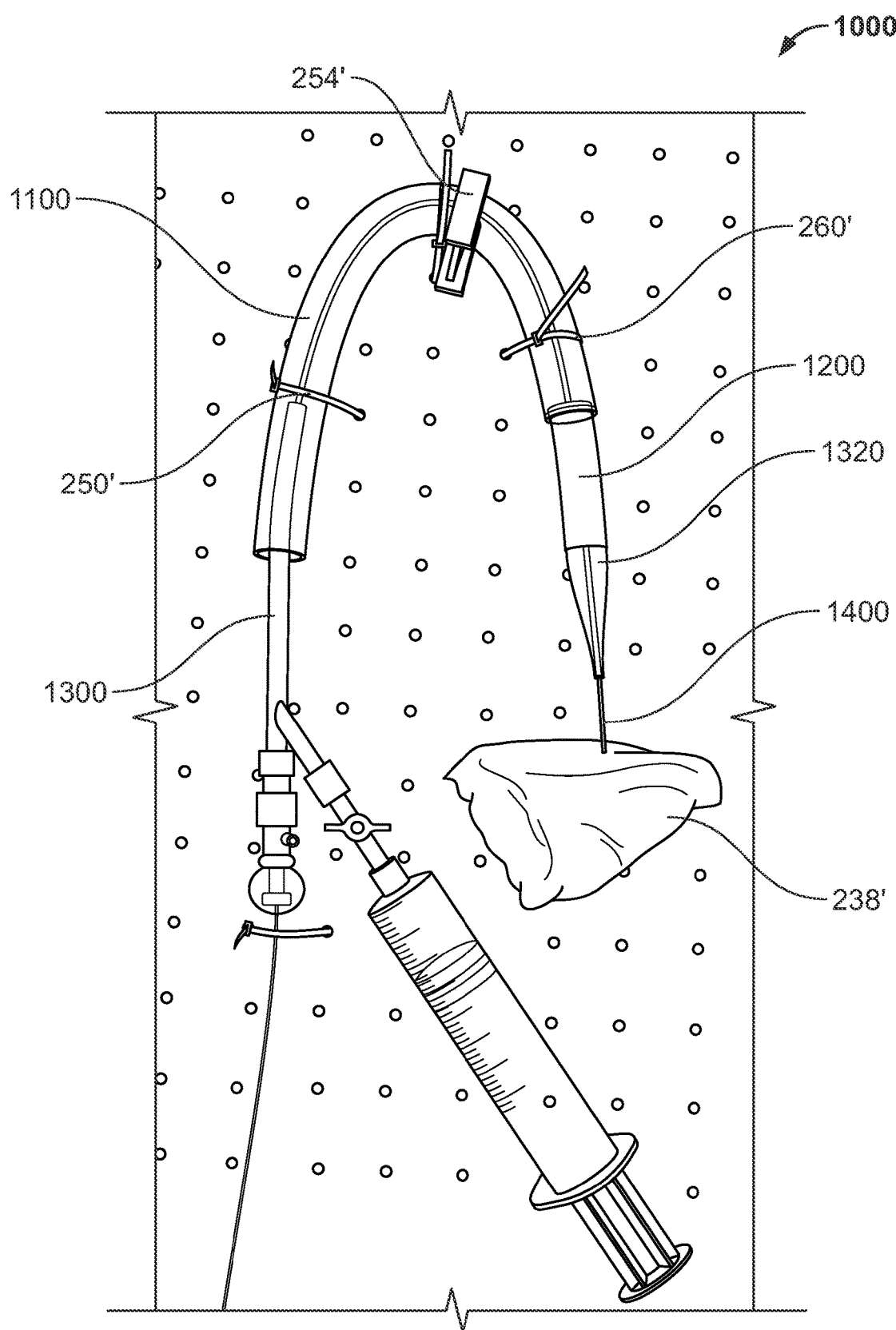
FIGS. 23-27 illustrate steps in a method of creating a transapical puncture from inside the heart.

FIG. 22 illustrates valve 110 implanted in heart 234 with anchor 210 seated at or near the apex 246 of heart 234. Tube 230 has been withdrawn from heart 234, through inferior vena cava 250 in the illustrated example, leaving valve 110 behind.

Generally, catheter 1000 is illustrated in FIGS. 23-27 attached to a board, with ties representing anatomical structures, including the exit of the inferior vena cava 250', the atrial septum 254', and the native mitral valve 260'. The ventricular wall 238' is represented by chicken breast. It should be understood that the model provided in FIGS. 23-27 may be delivered via the inferior vena cava or the superior vena cava, similar to the delivery routes described in connection with FIGS. 14 and 15.

Generally, guide catheter 1000 may include a positioning catheter 1100, which may be the outermost portion of guide catheter 1000. Positioning catheter 1100 may be used to "port" through the tortuous anatomy. Guide catheter 1000 may also include an epicardial pad or anchor catheter 1200, which may be positioned radially inward of positioning catheter 1100, and may function to hold and help deliver an anchor, including but not limited to the expandable tether anchor 210 described above. However, in some embodiments, the anchor catheter 1200 may be the outermost catheter and may also have a function similar to positioning catheter 1100, with the port catheter being omitted from guide catheter 1000. Still further, guide catheter 1000 may include a guide wire and/or needle 1400, which may be positioned radially inward of the balloon catheter 1300 and balloon 1320. The needle 1400 may include a sharp distal tip and may function to pierce through tissue. The needle 1400 may be solid or, in other embodiments, it may have a hollow interior. In one embodiment, the needle 1400 may be a sharpened guidewire having an outer diameter of about 0.035 inches. In another example, the needle 1400 may be a BRK™ Transseptal Needle, offered by Abbott Labs.

In use, the guide catheter 1000 may be advanced into the right atrium of a patient, for example via a transjugular delivery route through the superior vena cava, or a trans-femoral delivery route through the inferior vena cava. Regardless of the delivery route, the distal tip of needle 1400 is preferably positioned proximal of the distal tip of balloon 1320 during delivery so as to reduce the risk of unintentionally piercing any tissue during this delivery step. If positioning catheter 1100 is included in guide catheter 1000, the distal end of anchor catheter 1200 may be positioned proximal to, or aligned with, the distal end of the port catheter during this delivery step. The balloon 1040 may be partially or completely inflated during delivery, with the balloon extending beyond the distal end of positioning catheter 1100 (if included) and the distal end of anchor catheter 1200, with the inflated balloon providing an atraumatic leading surface or tip of the guide catheter 1000 during delivery. In order to provide a suitable atraumatic leading surface, the balloon 1320 may have a tapered shape when inflated.

A proximal end of positioning catheter 1100 may be coupled directly or indirectly to a handle that remains outside of the patient during the procedure, and the port catheter may include steering elements such as steering wires coupled to that handle to allow the user to steer the port catheter through the vasculature. If positioning catheter 1100 is omitted, the steering functionality may be provided on the anchor catheter 1200, although in some embodiments both the port catheter and the anchor catheter may include components to allow for steering. With the distal tip of the guide catheter 1000 being positioned in the right atrium (with or without use of steering of positioning catheter 1100), the distal tip may be positioned adjacent to the atrial septum 254'. Steering may be used to help position the distal tip of the guide catheter 1000 at the desired location on atrial septum 254' for a transseptal puncture. With the distal tip of guide catheter 1000 in the desired position adjacent the atrial septum 254', needle 1400 may be advanced distally beyond balloon 1320, with the needle piercing through the atrial septum 254'. The needle 1400 may be directly or indirectly coupled to the handle of the delivery system to allow for easy manipulation of the needle.

While needle 1400 is being advanced through atrial septum 254', it is preferable that balloon 1320 remains inflated, as the inflated balloon may provide additional stability (e.g. column strength) to the needle and help the needle resist deflecting or bending, although this is not required and the needle may be advanced while the balloon is partially or fully deflated. If needle 1400 punctures atrial septum 254' while balloon 1320 is deflated, the deflated balloon and needle may be advanced simultaneously during the puncturing, in order to position the deflated balloon within the transseptal puncture.

After needle 1400 has punctured the atrial septum 254', balloon 1320 is preferably deflated, for example by withdrawing fluid from the balloon via balloon catheter 1300. With balloon 1320 deflated, balloon catheter 1300 may be advanced distally (with or without corresponding motion of needle 1400) in order to position a portion of the deflated balloon within the punctured atrial septum 254'. If desired, the transseptal puncture may be increased in size to provide sufficient space for the passage of other portions of guide catheter 1000, such as positioning catheter 1100 (if used) and anchor catheter 1200. To increase the size of the transseptal puncture, balloon 1320 may be inflated while positioned within the transseptal puncture. If balloon 1320 is tapered, it may be advanced through the transseptal puncture while inflated in order to dilate the transseptal puncture to a size sufficient to receive therethrough other components of guide catheter 1000. Another option is to perform the dilation in a step-wise manner. For example, balloon 1320 may be inflated while the relatively small distal end of the balloon if positioned within the transseptal puncture. Balloon 1320 may then be deflated, and then further advanced a distance distally through the transseptal puncture, and re-inflated to further expand the transseptal puncture. This step-wise dilation may be performed in any number of desired steps. After the transseptal puncture is sufficiently dilated, positioning catheter 1100 (if included) and anchor catheter 1200 may be advanced into the left atrium.

It should be understood that, in other embodiments, a separate tool may be used to create the transseptal puncture, and the guide catheter 1000 may then be advanced through the atrial septum. However, it is generally preferable for guide catheter 1000 to create the septal puncture in order to reduce the required time for the procedure and the number of components involved.

Figure 24:
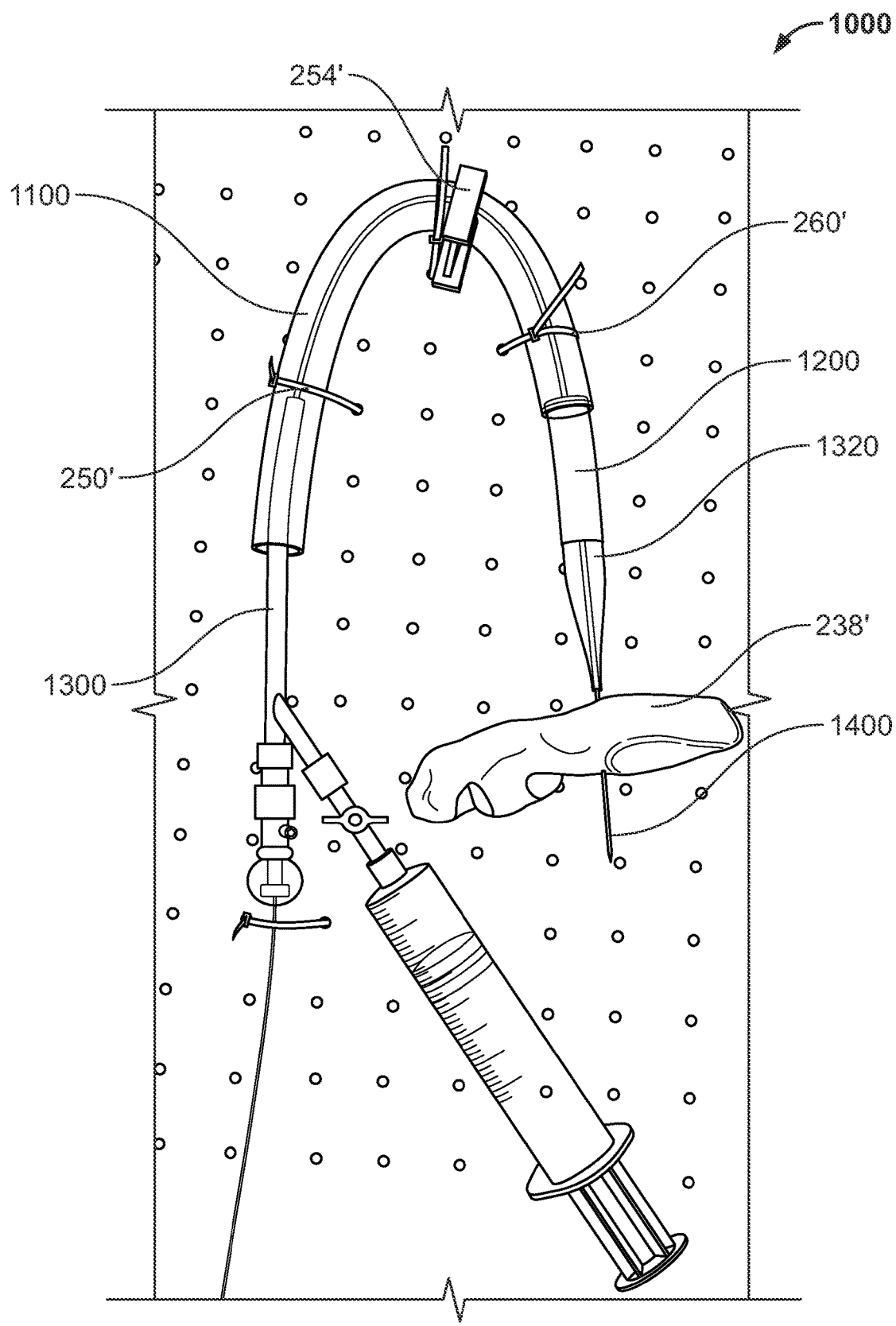

With the positioning catheter 1100 in the left atrium, the port catheter may be positioned, for example via the steering mechanism, so that the distal tip of the port catheter is substantially perpendicular to the plane of the annulus of the native mitral valve 260'. In other words, the distal end of positioning catheter 1100 is preferably positioned along an axis that is substantially co-axial with a longitudinal axis passing through the center of the annulus of the native mitral valve 260'. This relative positioning between positioning catheter 1100 and the native mitral valve 260' may provide an optimum positioning for further steps of the procedure. For example, while the positioning catheter 1100 is aligned with the central longitudinal axis of the native mitral valve 260', the anchor catheter 1200 may be advanced distally so that the anchor catheter passes through the native mitral valve and into the left ventricle. Further, the position of the positioning catheter 1100 may, at least in part, determine the position of the anchor delivered via the guide catheter 1000. Typically, it is desirable that the anchor is positioned substantially perpendicular to the plane of the annulus of the native mitral valve 260', as this orientation may desirable result in the tether attached to the anchor extending towards the longitudinal center of the mitral valve. As the anchor catheter 1200 is passing through the native mitral valve 260', it may be desirable for the balloon 1320' to be partially or fully inflated and extend beyond the distal tip of the anchor catheter, so that an atraumatic tip of the guide catheter 1000 is provided. This may avoid unintentionally damaging the patient's anatomy, and may also help avoid the distal tip of the guide catheter 1000 getting caught or otherwise entangled within the native chordae tendineae. Similarly, during the advancement of anchor catheter 1200 into the left ventricle, needle 1400 is preferably retracted within balloon 1320 so that the sharp distal tip of the needle is not exposed. With the tip of the balloon 1320 positioned adjacent or in contact with the ventricular wall 238', as shown in FIG. 23, needle 1400 may again be advanced distally beyond the balloon to pierce the ventricular wall, as shown in FIG. 24.

Figure 25:
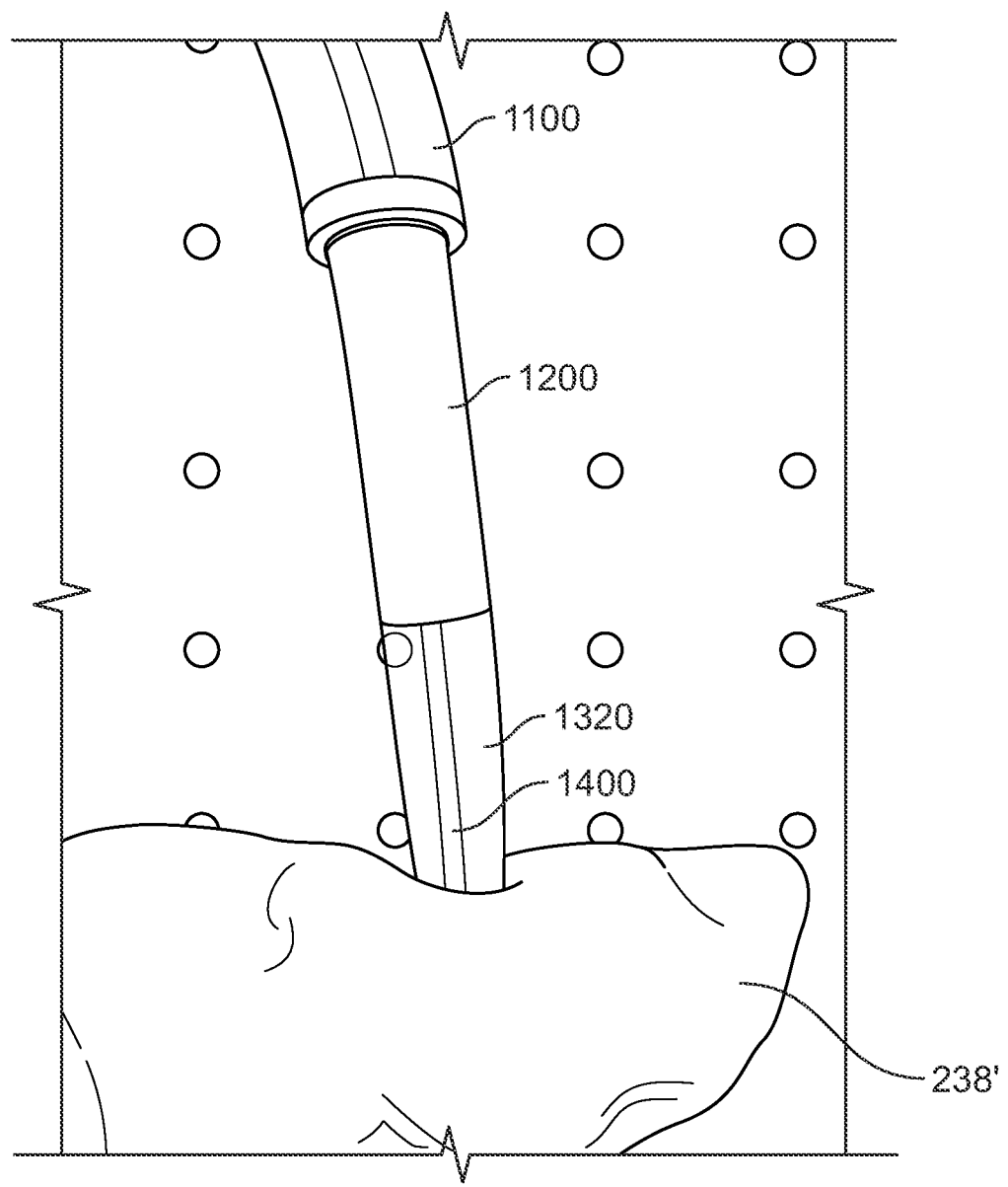

After needle 1400 begins to pierce the ventricular wall 238', or otherwise simultaneously with the needle piercing the ventricular wall, balloon 1320 and balloon catheter 1300 may be advanced distally with the needle, while the balloon is still inflated. Advancement of the balloon 1320 and needle 1400 may continue until heavy resistance is felt by the user. At this point, as shown in FIG. 25, balloon 1320 may be deflated, similar to the process described above for creating the transseptal puncture.

Figure 26:
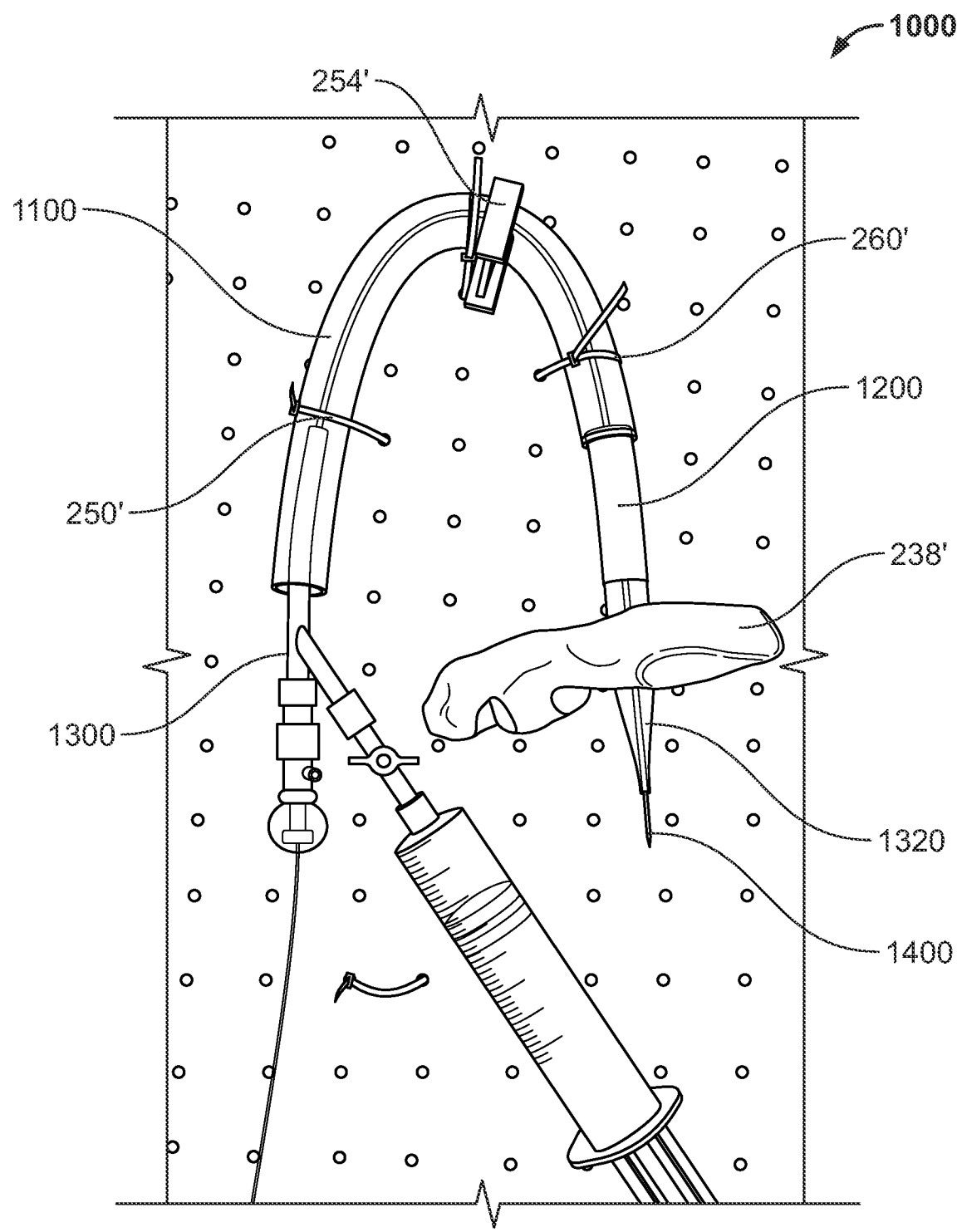
Figure 27:
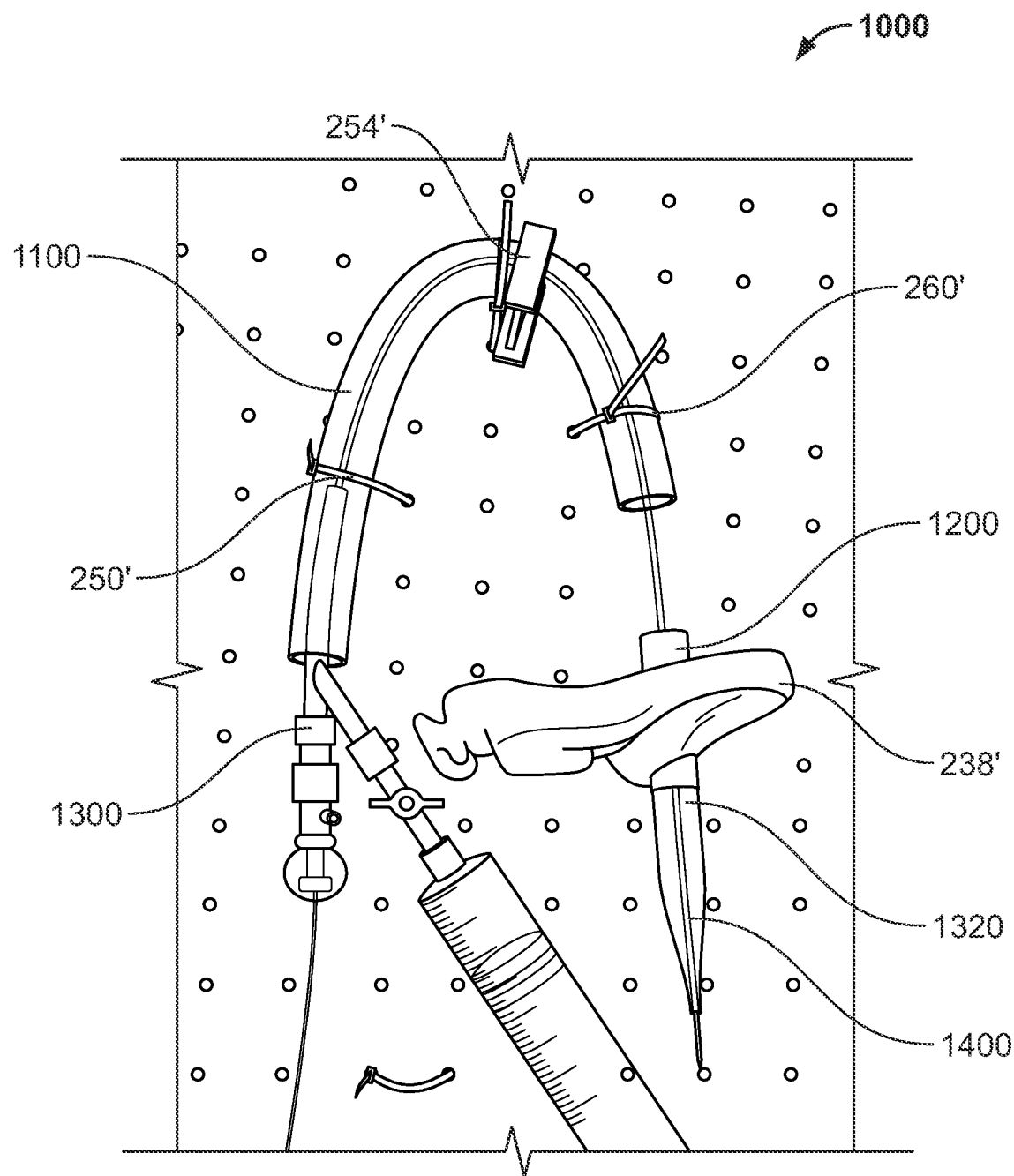

After balloon 1320 is deflated, the balloon may be further advanced into the myocardium of the ventricular wall 238' until a larger diameter portion of the balloon is surrounded by tissue of the ventricular wall. This advancement of balloon 1320 may be simultaneous with advancement of needle 1400. However, in other embodiments, it may be desirable to retract needle 1400 proximally before advancing the deflated balloon 1320 distally, in order to reduce the risk of the sharp tip of the needle passing beyond the ventricular wall 238' enough distance to damage other nearby tissue. Once a larger diameter portion of balloon 1320 is surrounded by tissue of the ventricular wall 238', the balloon may be inflated again to dilate the transapical puncture. As with the similar procedure described above for dilating the transseptal puncture, the transapical puncture of the ventricular wall 238' may be dilated one time, or multiple times in a step-wise manner until the transapical puncture is large enough, in this case to allow for passage of the anchor catheter 1200. The full dilation of the transapical puncture of the ventricular wall 238' is illustrated in FIG. 26, and passage of anchor catheter 1200 through the ventricular wall is illustrated in FIG. 27. Although anchor catheter 1200 is illustrated in FIG. 27 as having a proximal end that is positioned distal to the distal end of the positioning catheter 1100, in practice, the anchor catheter preferably has a length that extends to, or near, a handle configured to remain outside the patient during the procedure.

Although the step-wise dilation procedures is described above for both the transseptal puncture and the transapical puncture, it may not be needed in both, or either, procedure. However, the ventricular wall 238' near the apex of the heart is typically much thicker than the atrial septum 254', so the step-wise dilation may be more likely to be used during the transapical puncture than the transseptal puncture.

After a portion of the anchor catheter 1200 has passed through the ventricular wall 238', balloon 1320 may be deflated and pulled proximally through the anchor catheter, leaving the distal end of the anchor catheter open so that an anchor may be passed through the anchor catheter for positioning at the apex of the left ventricle. In some embodiments, the anchor may be an expandable anchor similar or identical to anchor 210, which may be kept in a collapsed condition within anchor catheter 1200 just proximal to the balloon 1320 during the delivery procedure.

Figure 28A:
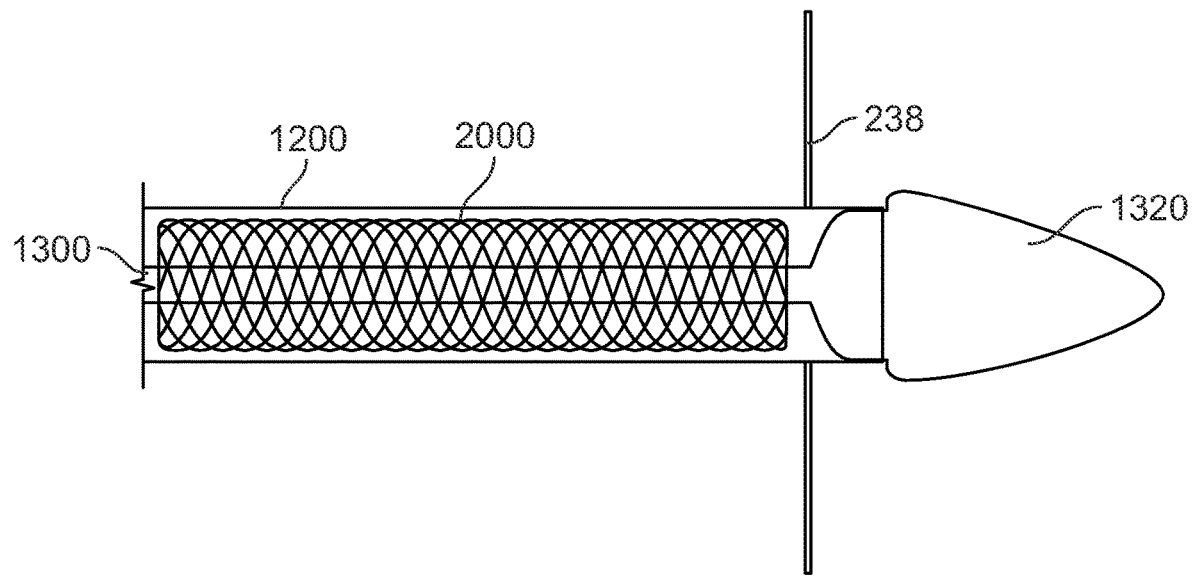
FIGS. 28A-D illustrate steps in a method of deploying an anchor from within the heart using one embodiment of a delivery catheter.
Figure 28B:
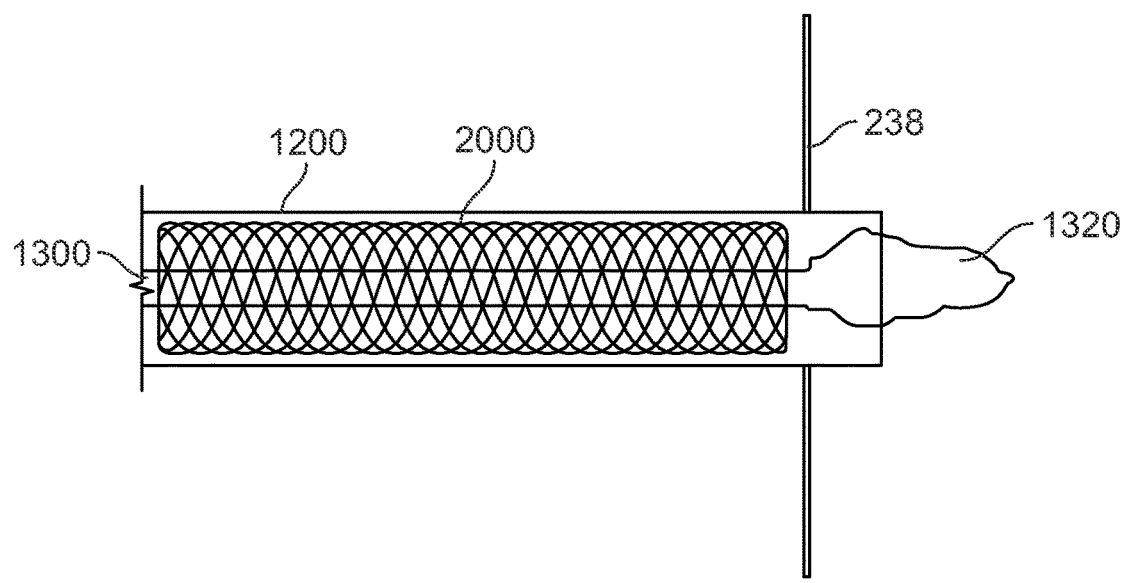
Figure 28C:
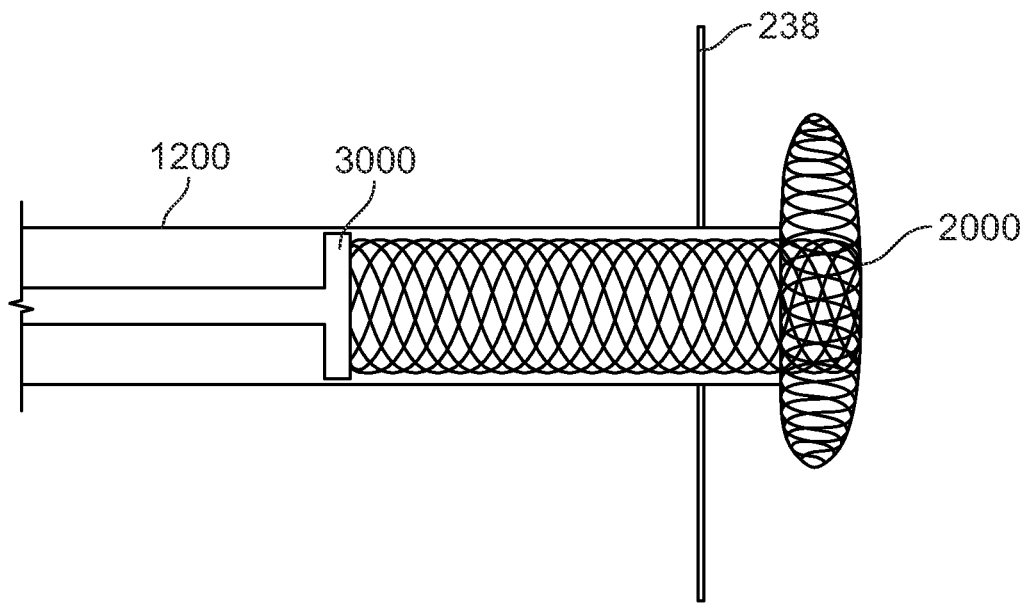
Figure 28D:
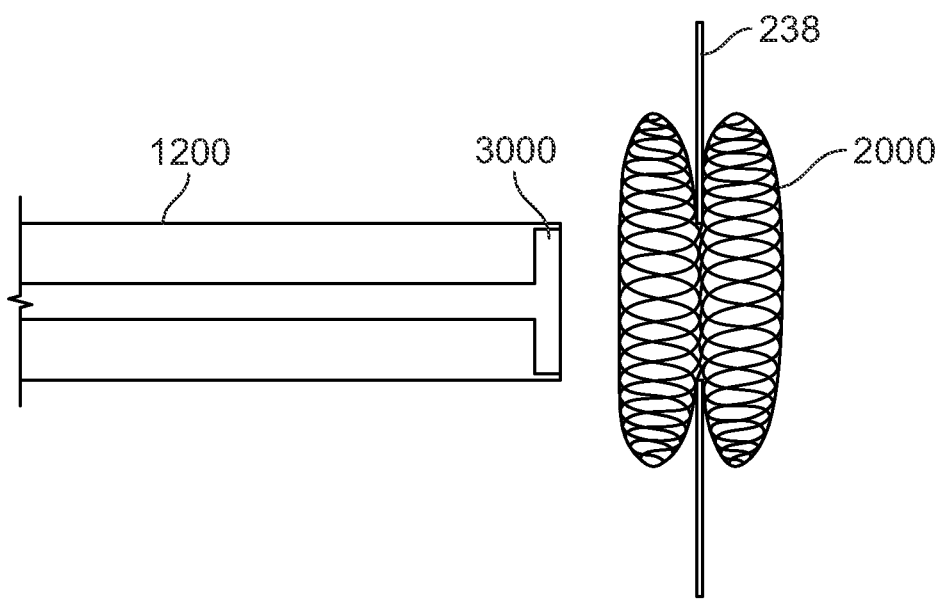

FIGS. 28A-D are highly schematic illustrations of the release of an expandable anchor 2000 that may be generally similar to anchor 210. FIG. 28A illustrates anchor catheter 1200 extending through the ventricular wall 238 with the balloon 1320 of balloon catheter 1300 still inflated, and anchor 2000 in a collapsed condition with the balloon catheter passing through the interior of the anchor. FIG. 28B shows balloon 1320 having been deflated, for example by withdrawal of fluid via balloon catheter 1300. After balloon 1320 is deflated, the balloon and balloon catheter 1300 may be removed proximally through anchor catheter 1200, through the inside of the collapsed anchor 2000. As shown in FIG. 28C, anchor 2000 (or a portion thereof) may be deployed from the distal end of the anchor catheter 1200 on the exterior surface of the ventricular wall 238. This may be accomplished by any suitable method. For example, a push rod 3000 may be positioned proximal the anchor 2000, and the push rod may be pushed distally and/or the anchor catheter 1200 may be pulled proximally to force the anchor out of the open distal end of the anchor catheter. Push rod 3000 may include a shaft with an interior lumen through which balloon catheter 1300 and/or balloon 1320 may be retracted, and within which needle 1400 may be positioned. Needle 1400 is omitted from FIGS. 28A-D for clarity of illustration. The anchor 2000 may be continued to be deployed until it fully exits the anchor catheter 1200, as shown in FIG. 28D. Although not shown in FIG. 28D, a tether similar to tether 226 may be fixed to anchor 2000 and extend proximally through a portion of, or all of, guide catheter 1000. That tether may be used as a rail over which a prosthetic heart valve, which may be similar to prosthetic heart valve 110, may be delivered. Instead of having the tether fixedly coupled to the prosthetic heart valve, the prosthetic heart valve may include hooks or a similar feature on a portion of the prosthetic heart valve, such as a portion of an inner stent similar to clamping portion 144. The hooks may be directional so that the prosthetic heart valve may be advanced distally over the tether, but not translated proximally. Thus, when the prosthetic heart valve is deployed in the native mitral valve 260, those hooks or similar features may prevent the prosthetic heart valve from migrating toward the left atrium during use. Any excess length of the tether extending proximally to the prosthetic heart valve may be removed from the body, for example by cautery or another suitable method.

Figure 29A:
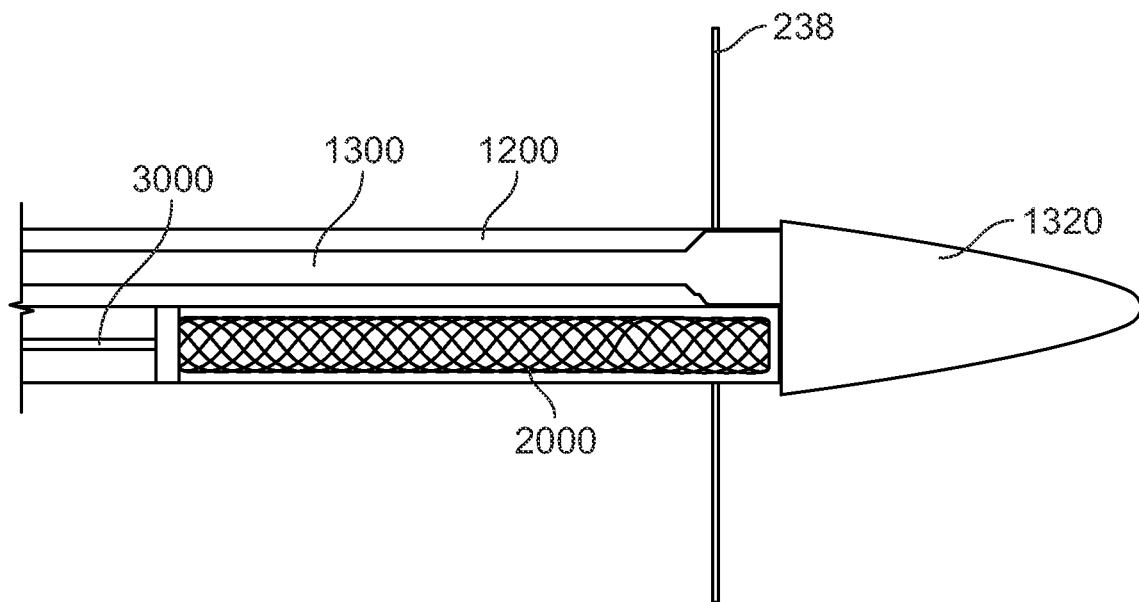
FIGS. 29A-E illustrate steps in a method of deploying an anchor from within the heart using another embodiment of a delivery catheter.
Figure 29B:
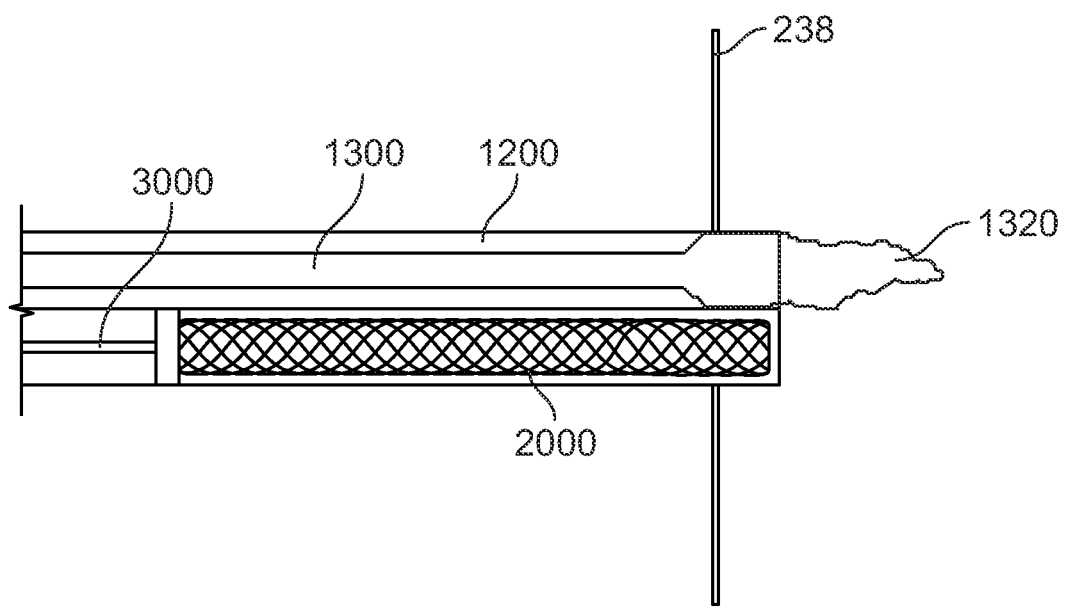
Figure 29C:
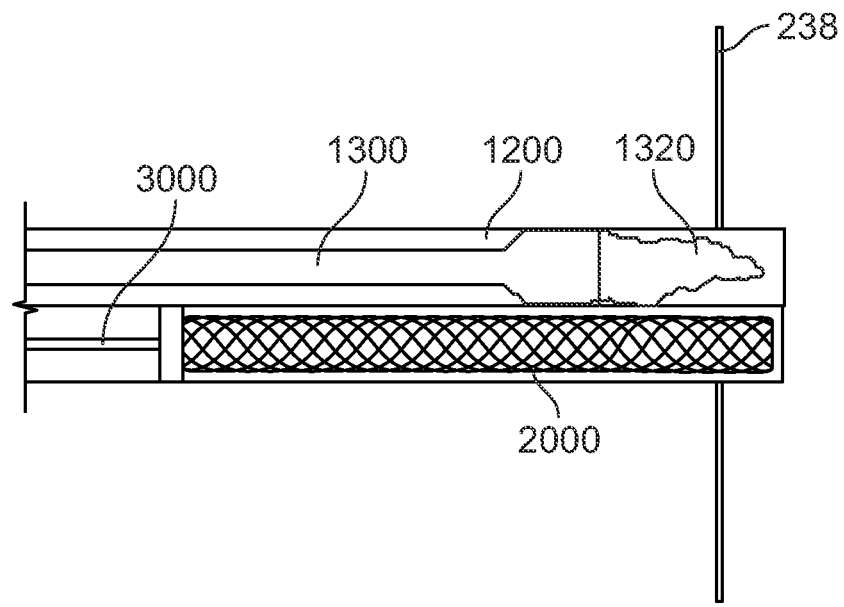
Figure 29D:
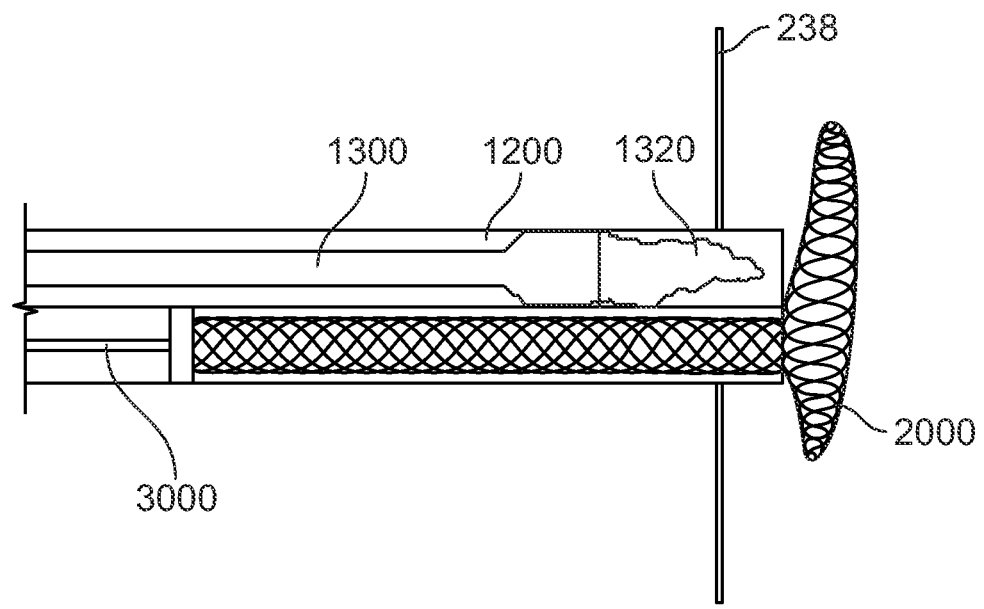
Figure 29E:
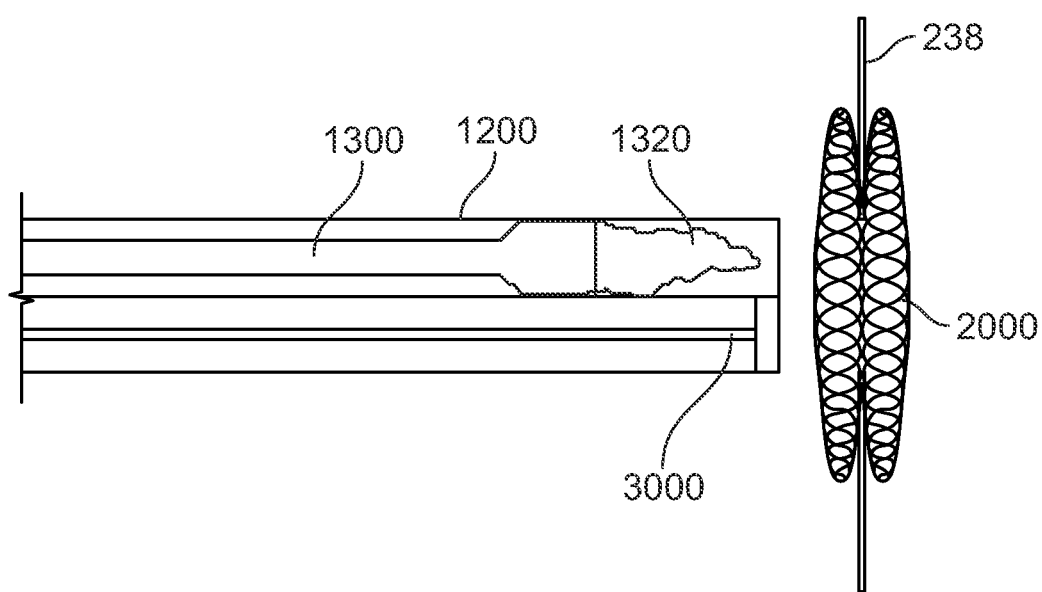

In another embodiment, shown in FIGS. 29A-E, the anchor catheter 1200 may include at least two separate lumens, a first lumen receiving the anchor 2000 and other components, such as push rod 3000, with the balloon catheter 1300 extending through the second lumen. FIG. 29A illustrates anchor catheter 1200 extending through the ventricular wall 238 with the anchor 2000 collapsed in the first lumen, the balloon catheter 1300 extending through the second lumen, and the balloon 1320 still inflated. FIG. 29B shows balloon 1320 having been deflated, after which the balloon and balloon catheter 1300 may be removed proximally through the second lumen of anchor catheter 1200, either partially or fully. FIG. 29C illustrates balloon 1320 and balloon catheter 1300 having been withdrawn into the second lumen of anchor catheter 1200. As shown in FIG. 29D, anchor 2000 (or a portion thereof) may be deployed from the distal end of the anchor catheter 1200 on the exterior surface of the ventricular wall 238. In the illustrated embodiment, push rod 3000 extends through the first lumen of anchor catheter 1200. The push rod 3000 may be pushed distally and/or the anchor catheter 1200 may be pulled proximally force the anchor out of the open distal end of the anchor catheter. As with FIGS. 28A-D, needle 1400 is omitted from FIGS. 29A-E for clarity of illustration. The anchor 2000 may be continued to be deployed until it fully exits the anchor catheter 1200, as shown in FIG. 29E. As with the embodiment shown in FIGS. 28A-D, a tether may extend from anchor 2000, and that tether may be coupled to a prosthetic heart valve that is deployed in the native mitral valve 260 to help prevent the prosthetic valve from migrating into the left atrium.

Other apparatus and methods may also be suitable for assisting in delivering a tether anchor to the ventricular apex without requiring an incision in the patient's chest. As further explained below, the apparatus and methods described herein may provide a mechanical advantage to perform a ventricular apical incision in a fully transcatheter procedure. The apparatus, methods, and descriptions above can be used in combination with the following disclosure.

Generally, catheters, such as catheter 4000 and catheter 5000, are illustrated in FIGS. 30-37.

FIG. 30 illustrates a cross section of a distal end portion of catheter 4000 suitable for delivery and deployment of an expandable tether anchor to the ventricular apex. Although not illustrated in FIGS. 30, guide catheter 4000 may contain the components described in connection with other delivery catheters above, such as needle 1400, positioning catheter 1100, epicardial pad or anchor catheter 1200, and/or balloon catheter 1300 and balloon 1320. Catheter 4000 can be for example a guide catheter. FIG. 30 illustrates a cross section view taken longitudinally along the catheter length. Cather 4000 may contain a straightener spring 4010, a positioning catheter 4020, an anterior pull wire 4030, a balloon 4040, an exterior surface 4050, and an anchor catheter 4099. Without limitation, catheter 4000 can contain additional components, such as additional pull wires, as further explained below. It should be understood that in some examples, the various catheters can be combined into a single catheter. For example, positioning catheter 4020 and anchor catheter 4099 may be combined into one catheter.

Straightener spring 4010 can be made of one or more springs or other suitable biasing elements of suitable materials and mechanical properties to provide catheter 4000 with self-straightening characteristics. For example, the spring can be made of a metal or metal alloy, and of a specific desired spring constant to allow catheter 4000 to tend to self-straighten during the transcatheter delivery of the catheter 4000. In other words, when spring 4010 is relaxed, the distal end of catheter 4000 is substantially straight. If the catheter 4000 is manipulated to steer the distal end of the catheter, for example by pulling the anterior pull wire 4030 to deflect the distal tip of catheter 4000 relative to the remainder of the catheter, spring 4010 becomes extended (or compressed). If force on the anterior pull wire 4030 is reduced or released, spring 4010 will tend to cause the distal end of catheter 4000 to return to the substantially straight condition. Further, spring 4010 can be made of any shape, such as a compression spring, a torsion spring, or a drawbar spring. It is also possible that straightener spring 4010 be made of an electrically sensitive or electrically reactive material, which allows the mechanical properties of spring 4010 to be changed through an application of electricity through the spring. An application of electricity in this manner can allow for the spring to change its elasticity or resistance to force, thereby allowing for the steerability of or shape taken by catheter 4000 to be modified. Electricity could be delivered through, for example, suitable electrical connections of low voltage and current positioned within guide catheter 4000. The straightener spring 4010 can be placed in the tip of the guide catheter 4000.

Figure 31:
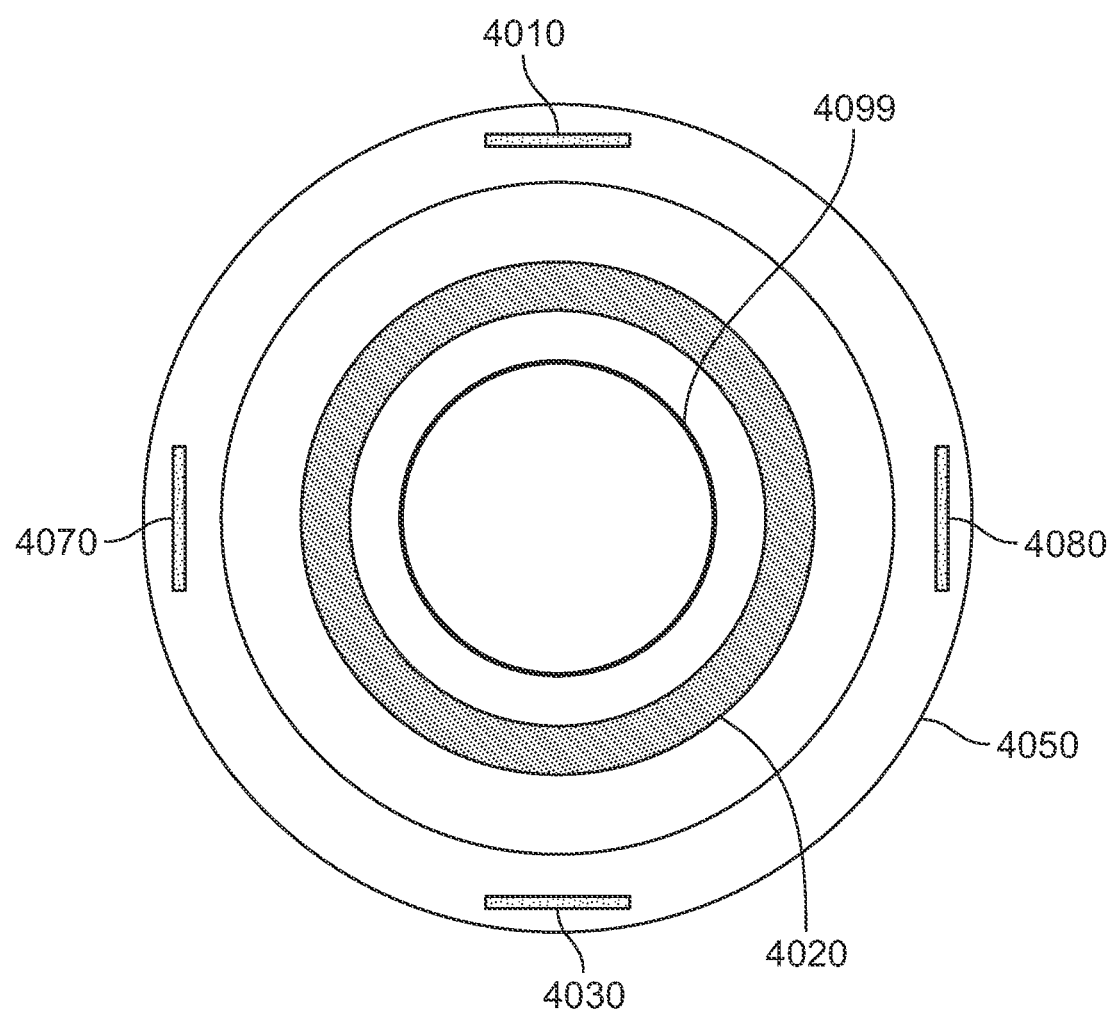
FIG. 31 illustrates a transverse cross section of the catheter of FIG. 30.

Anterior pull wire 4030 may be a wire which is mechanically connected to guide catheter 4000. Anterior pull wire 4030 can be made of any suitable material which allows for the catheter 4000 to be steered through applying tension on the pull wire. For example, when it is desired to deflect a distal end of the delivery catheter downward (in the view of FIG. 30) or away from the balloon 4040, additional tension can be applied to anterior pull wire 1030. Materials, techniques, and commercially available types of pull wires which can be used to make up anterior pull wire 4030 are well known in the art. Although not illustrated in FIG. 30, guide catheter 4000 can also contain similar pull wires, such as a lateral pull wire 4070 and a medial pull wire 4080 (FIG. 31), located within and connected to the catheter 4000 to provide additional steerability and control of guide catheter 4000. It should be understood that any of the pull wires may be physically coupled to a distal end portion of catheter 4000 near a distal tip, with the pull wire extending proximally through the catheter toward a handle or similar device that remains outside the patient's body, with manipulation of the handle allowing the pull wires to be pulled (or tensioned) or for tension to be released to steer the distal end of the catheter 4000 in the desired direction(s). In one example, as illustrated in FIG. 31, the pull wires may extend through pull-wire lumens formed in a wall of the catheter 4000. Although some embodiments may include a posterior pull wire (which may be positioned opposite the anterior pull wire 4030), the inclusion of balloon 4040, described in greater detail, may hinder the ability to include such a posterior pull wire. Rather, as shown in FIG. 30, the spring 4010 will tend to reverse the action of anterior pull wire 4030 once tension on the anterior pull wire is released. Thus, spring 4010 may provide a similar functionality as a posterior pull wire would provide, without the need to include such a posterior pull wire.

Balloon 4040 can be integrated into catheter 4000. Balloon 4040 can be made of a semi-compliant material. Any suitable material can be used to make balloon 4040, such as, without limitation, Pebax or higher-durometer polyurethane materials. When balloon 4040 is made from a semi-compliant material, it allows balloon 4040 to be inflated and for the guide catheter 4000 to be stabilized across a variety of heart geometries. The compliance or semi-compliance of the balloon 4040 may also help the balloon conform to the shape of the anatomy it contacts (e.g. an interior wall of the left atrium), which may help maximize surface area contact between the inflated balloon 4040 and the anatomy. As further illustrated below, balloon 4040 can be integrated into the catheter 4000 such that a portion of the catheter is substantially made of the balloon 4040. This allows the balloon to be inflated through mechanisms contained within the catheter 4000. For example, balloon 4040 can be inflated or deflated through balloon inflation lumen 4060, which can be contained within catheter 4000. The balloon can be inflated using any suitable fluid, such as for example, a saline solution. Balloon 4040 may be positioned a spaced distance from the distalmost end of catheter 4000. In the illustrated embodiment, 4040 is positioned proximal to the spring 4010.

Catheter 4000 can contain an exterior surface, 4050. Exterior surface 4050 can be the exterior surface and be formed by any suitable material which are known in the art for forming catheters. Exterior surface 4050 can be formed through an external wall of catheter 4000 of fixed or varying thickness. Various components, such as the anterior pull wire 4030, can be attached to the external wall of catheter 4000. In the illustrated embodiment, balloon inflation lumen 4060 may be formed in the catheter wall that defines the exterior surface 4050, similar to the pull wire lumens shown and described below in connection with FIG. 31. The balloon inflation lumen 4060 may extend substantially the entire length of catheter 4000, so that a first end of the balloon inflation lumen 4060 located at or near a proximal end of the catheter 4000 is in sealed fluid communication with the interior of balloon 4040. Thus, as is explained in greater detail below, as catheter 4000 is advanced to the left atrium, the balloon 4040 is in a deflated condition so that the balloon 4040 does not increase the profile of catheter 4000. In the deflated condition, balloon 4040 may form a portion of the exterior surface 4050 of the catheter 4000. Once the distal end of the catheter 4000 is in the desired position and orientation within the left atrium, inflation media may be pushed through the balloon inflation lumen 4060 to inflate balloon 4040 to the desired extent, the purpose of which is described in greater detail below.

FIG. 31 illustrates a transverse cross section view of the distal tip of guide catheter 4000. Illustrated in FIG. 31 is straightener spring 4010, anterior pull wire 4030, lateral pull wire 4070, and medial pull wire 4080. FIG. 31 also illustrates the positioning catheter 4020 positioned radially inside the guide catheter 4000. FIG. 31 also illustrates anchor catheter 4099 positioned radially inside positioning catheter 4020. Lateral pull wire 4070 and medial pull wire 4080 can be made in a manner similar to anterior pull wire 4030. In addition, lateral pull wire 4070 and medial pull wire 4080 can be tensioned. By applying a force or tension to one or more of the pull wires, e.g. medial pull wire 4080, the distal end of catheter 4000 can be deflected in the desired direction(s). By modifying the angle of the tip of the guide catheter 4000, the position of the positioning catheter 4100 can be modified. The various pull wires can run substantially along the length of the guide catheter 4000. The pull wires (e.g. lateral pull wire 4070), can be attached to an external apparatus on one end to be more easily tensioned. Straightener spring 4010, anterior pull wire 4030, lateral pull wire 4070, and medial pull wire 4080 can be positioned in a manner such that they are roughly circumferentially equidistant and equiangular from one another, that is, that they are placed at substantially 90 degree angles from one another. Although three pull wires are illustrated in FIG. 31, guide catheter 4000 can contain additional pull wires in other geometries. For example, a configuration with four pull wires and a spring can be created, where the four pull wires are placed roughly circumferentially equidistant and equiangular from one another, such as at 72 degrees from one another. Additional pull wires allow for additional combinations of various tensions to be applied, allowing for additional degrees of freedom in deflecting the guide catheter 4000. Other configurations and linear combinations of springs and pull wires are within the scope of this disclosure.

As with other catheters described herein, positioning catheter 4020 may be positioned radially within and translatable relative to guide catheter 4000. Positioning catheter 4020 may contain the anchor catheter 4099 radially within the positioning catheter 4020. In some embodiments, the features of the anchor catheter 4099 may be combined within positioning catheter 4020. It is to be understood that guide catheter 4000, positioning catheter 4020, and anchor catheter 4099 may have one or more features, structures, or functions described herein. In some examples, guide catheter 4000 may have generally similar structure and function as guide catheter 1000, positioning catheter 4020 may have generally similar structure and function as positioning catheter 1100, and anchor catheter 4099 may have a generally similar structure and function as anchor catheter 1200.

Figure 32:
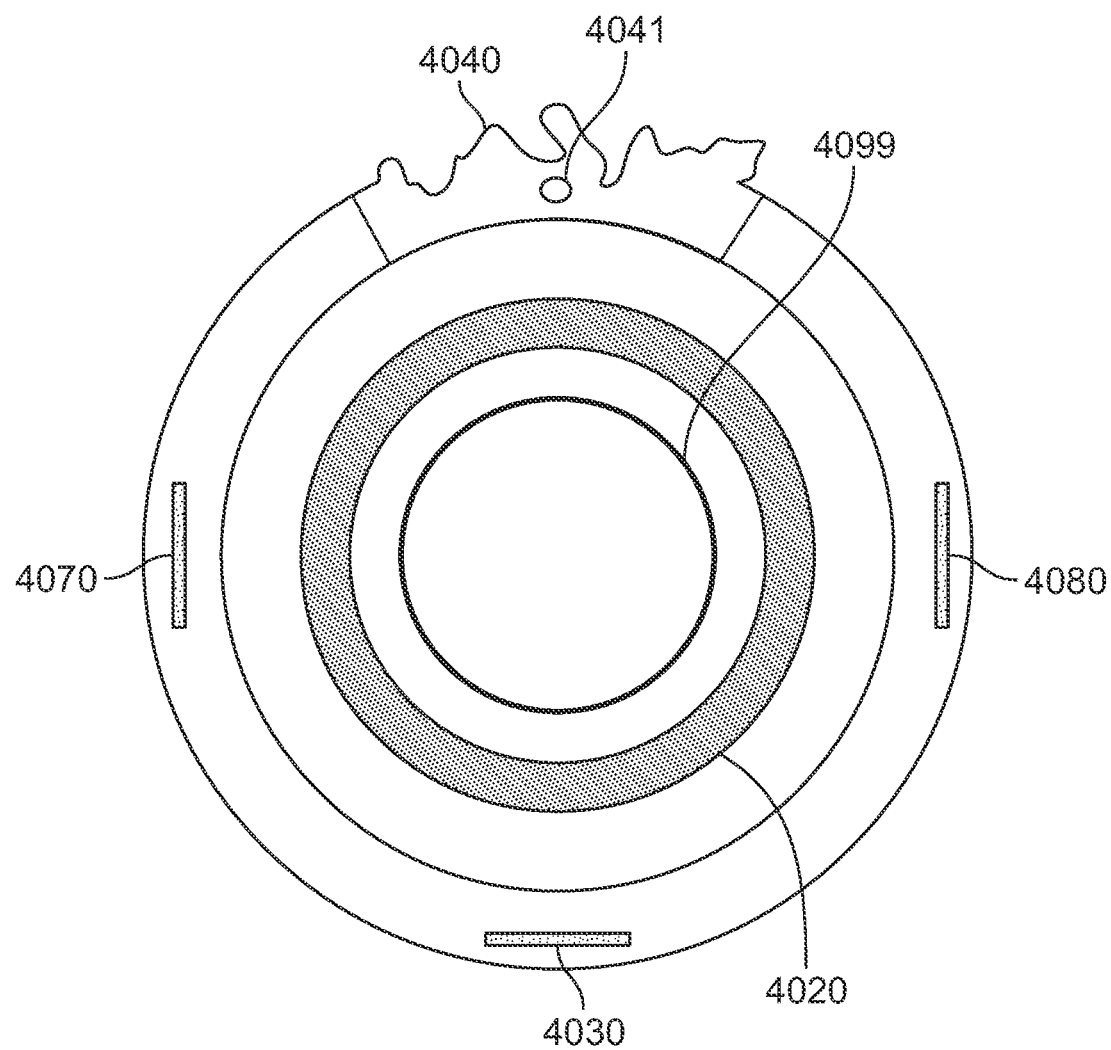
FIG. 32 illustrates a transverse cross section of the catheter of FIG. 30 at a cross-section close to an inflatable balloon portion.

FIG. 32 illustrates a cross section view of a portion of the delivery catheter near the position of the delivery catheter which contains balloon 4040. Illustrated in FIG. 32 is balloon 4040 in a deflated condition, anterior pull wire 4030, lateral pull wire 4070, and medial pull wire 4080. Balloon 4040 can contain an opening to allow a solution to enter and expand the balloon 4040, such as port 4041, which may be in fluid communication with balloon inflation lumen 4060 (illustrated in FIG. 30).

Figure 33:
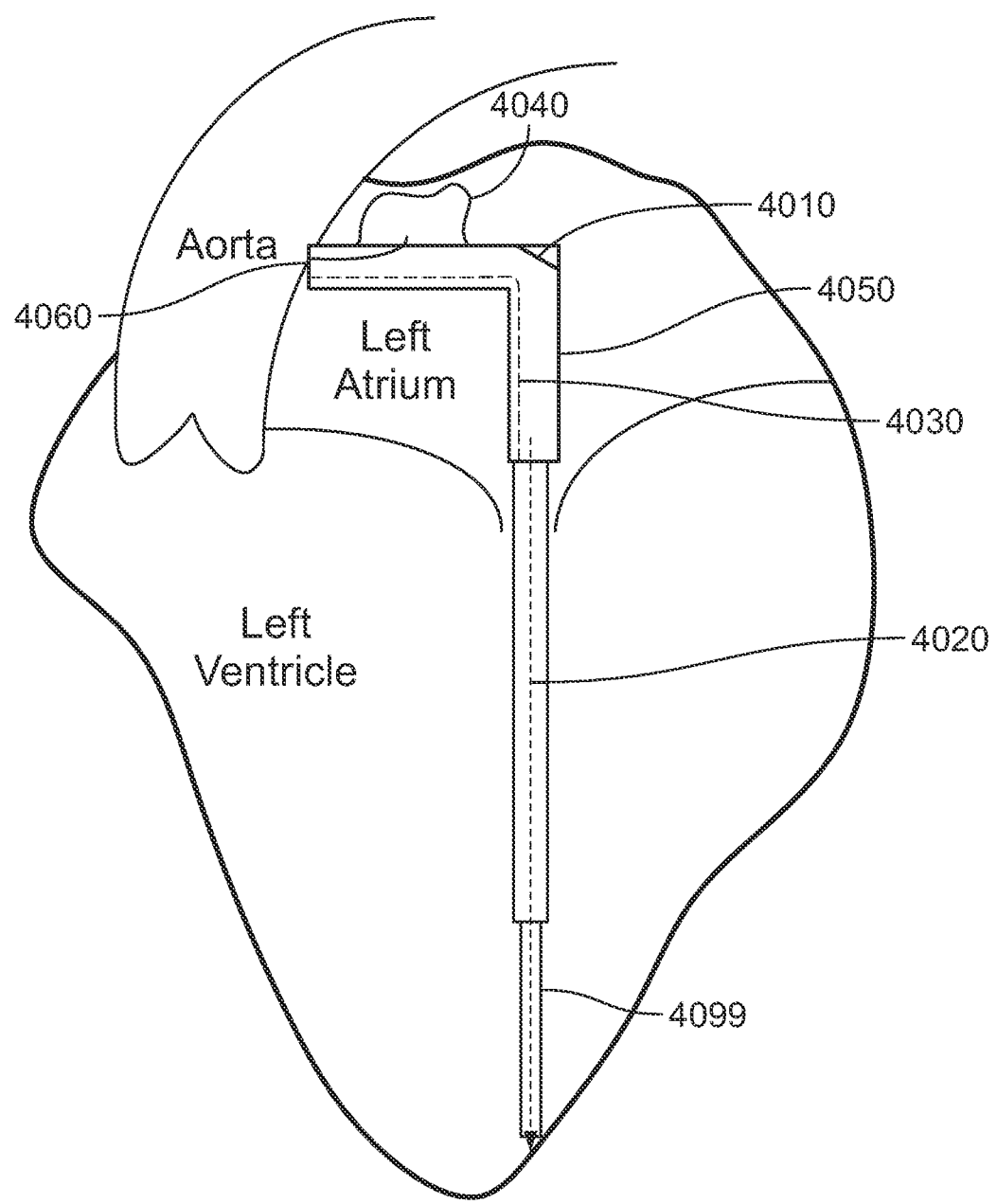
FIG. 33 illustrates a transverse cross section of the catheter and heart during operation of the catheter.

FIG. 33 illustrates catheter 4000 during its use in creating a ventricular incision through the ventricle wall from the left ventricle. In a transcatheter prosthetic mitral valve implantation in which an outflow end of the prosthetic mitral valve is coupled to an epicardial pad or anchor via a tether, it may be desirable for the tether to extend in a direction that is orthogonal to the plane of the mitral valve annulus. Catheter 4000 may be delivered via any of the routes described above to reach the right atrium, and then be passed into the left atrium through a transseptal incision. The transseptal incision may be formed by any of the methods described above. When catheter 4000 enters the left atrium, the positioning catheter 4020 is preferably still positioned within the catheter 4000. The anterior pull wire 4030 may be tensioned to deflect the distal tip of the catheter toward the mitral valve annulus so that the distal tip of the catheter is substantially coaxial to the mitral valve annulus, extending in a direction orthogonal to the plane of the mitral valve annulus. As with embodiments described above, with the catheter 4000 in the desired position and orientation, the positioning catheter 4020 may be advanced through the native mitral valve until a distal tip of the positioning catheter is in contact with or adjacent the wall of the left ventricle. Similar to catheter 1000, a needle may then be advanced from the positioning catheter 4020 to create an incision in the ventricular wall so that an expandable anchor may be passed through the ventricular wall. However, as a needle (or similar device) begins to contact the left ventricular wall, an opposite force is exerted by the wall onto the needle. Depending on the material and the geometry of the needle, the opposing force may tend to cause the needle to deflect and/or to push the guide catheter 4000 toward the top of the left atrium. In order to counteract this tendency, prior to contacting the left ventricular wall with the needle, inflation media may be passed into balloon 4040 through balloon inflation lumen 4060. The compliance of the balloon will help the balloon 4040 conform to the interior geometry of the left atrium, even despite variations in atrial shapes and sizes from patient to patient. Once the balloon 4040 is inflated to the desired amount, the contact between the balloon 4040 and the interior surfaces of the left atrium provide a stabilizing force to counteract forces resulting from the needle contacting the left ventricular wall. In other words, contact between the inflated balloon 4040 and the interior left atrial wall help stabilize the needle as it begins to pierce and pass through the left ventricular wall. After the needle pierces the ventricular wall, the expandable anchor and prosthetic mitral valve may be deployed and implanted in the same or similar fashion as described in connection with embodiments described above.

FIGS. 34 to 37 illustrate apparatus and methods which may be used to assist in delivering a tethered prosthetic mitral valve, either alone or in combination with any of the features described above. FIGS. 34 to 37 illustrate apparatus and methods which may be used to perform imaging for a transapical puncture of the myocardium from within the left ventricle, eliminating the need to perform a mini thoracotomy or other incision in the chest wall. Without limitation, techniques, methods, and apparatus may be used to perform imaging for the transapical incision, which may be completed entirely via transseptal and/or transfemoral access. One advantage of the apparatus and methods described below is that they may facilitate the apical puncture being performed from the ventricle side of the heart. Further, another advantage of the apparatus and method described below is that they facilitate an orthogonal alignment with the annular plane. As noted above, if a prosthetic mitral valve is to be anchored via a tether extending from the prosthetic mitral valve to an anchor (such as the expandable epicardial anchor described above), it is typically desirable for the tether to extend in a direction that is orthogonal to the plane of the native mitral valve annulus, and in a direction substantially coaxial with the native mitral valve annulus. Thus, if a transapical puncture is performed from within the left ventricle, it is typically desirable that the device used to perform the transapical puncture to be delivered toward the ventricle wall in a direction that is coaxial with the native mitral valve annulus, in a direction orthogonal to the plane of the mitral valve annulus. Without limitation, these methods and techniques can be advantageously used to align instrumentation before creating a poke or incision in the heart.

Figure 34:
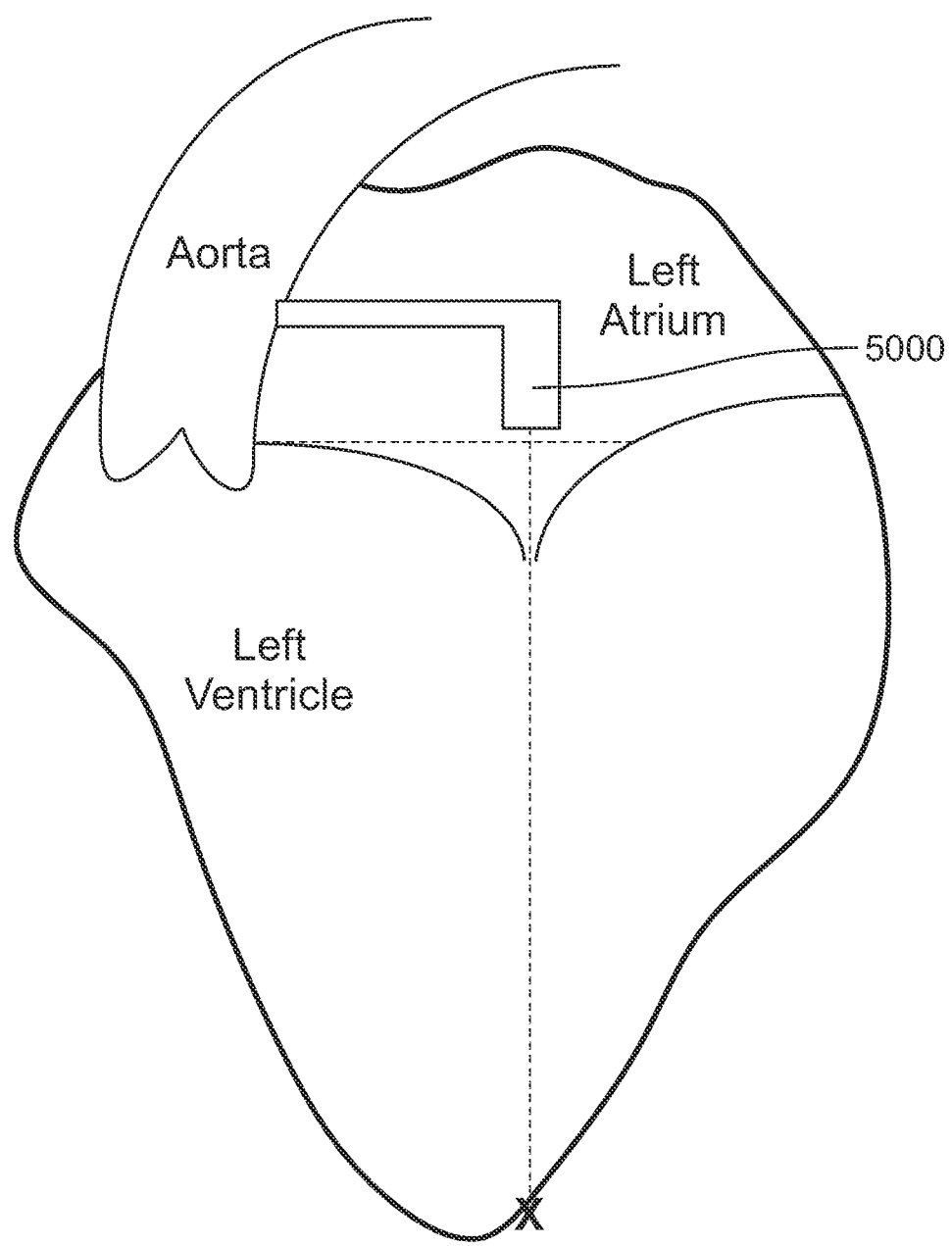
FIG. 34 illustrates a highly schematic view of a catheter during a step of deploying an anchor from within the heart.

FIG. 34 illustrates a simplified cross section of the left side of the heart. Detailed in FIG. 34 are simplified portions of the heart illustrated, such as the aorta, left ventricle, and left atrium. Also illustrated in FIG. 34 is a catheter 5000 (e.g. any catheter disclosed above, such as catheter 1000 or catheter 4000 or a guide catheter). A distal end of catheter 5000 is illustrated in FIG. 34 as having crossed the septum separating the left atrium and the right atrium (right atrium not illustrated in FIG. 34), and having been deflected downward toward the left ventricle. Catheter 5000 may be capable of various types of deflection and/or steering, such as in the anterior, posterior, medial, and/or lateral directions. Although not illustrated in the simplified FIG. 34, the guide catheter 5000 can also contain other components described within this disclosure, such as an inner catheter that may be translated relative to the illustrated catheter, and a needle or other puncture device that may translate relative to the inner catheter. A dotted line running along the left atrium illustrates an annular plane. FIG. 34 also illustrates a second dotted line, extending from the native mitral valve annulus to a wall of the left ventricle illustrating a path, which is substantially orthogonal to the plane of the mitral valve annulus. This second dotted line represents a desired path for a device to travel from the outer guide catheter 5000 to the ventricle wall (or to a position just adjacent the ventricle wall) as part of the transapical puncture procedure. In other words, the second dotted line is positioned substantially coaxial with the native mitral valve annulus, and extends substantially orthogonal to the plane of the native mitral valve annulus.

Figure 35:
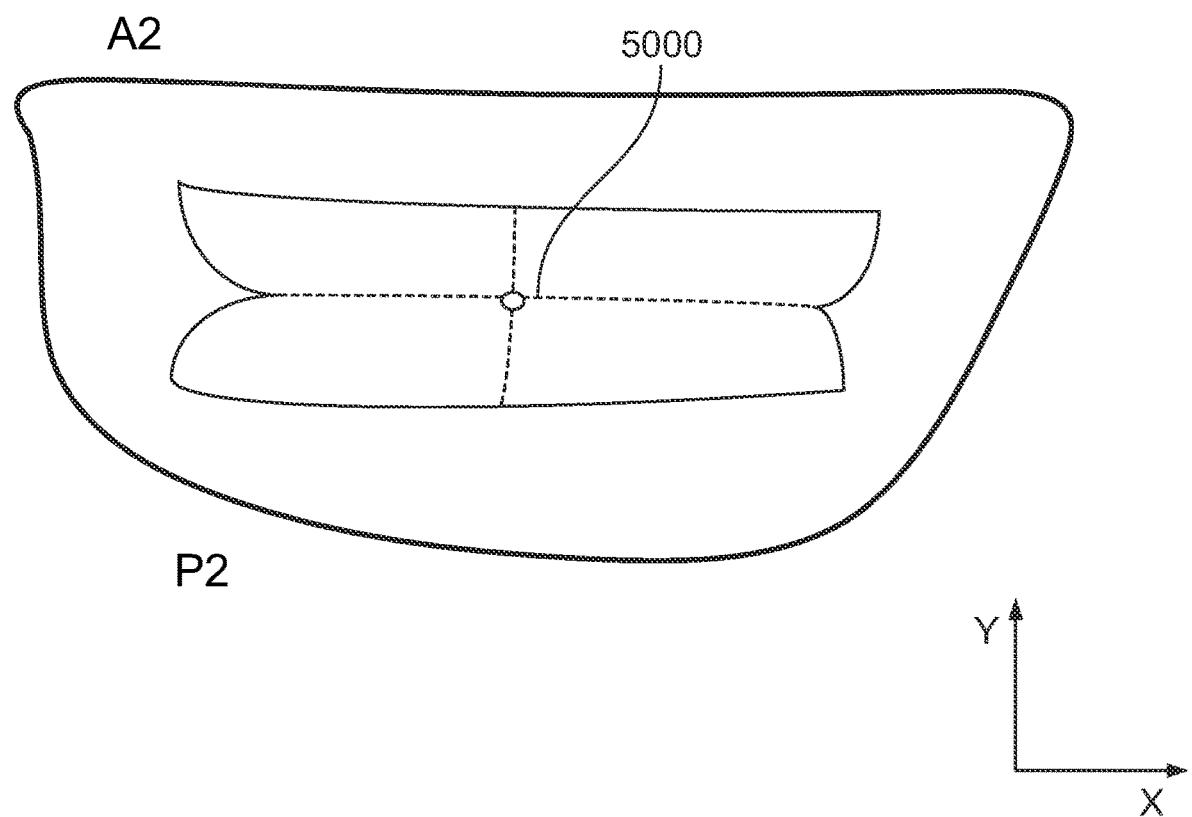
FIG. 35 illustrates a top-view of a mitral annulus with a catheter extending therethrough.

FIG. 35 illustrates a simplified top view of the native mitral valve annulus, that is, as viewed from a cross section perpendicular to the superior-inferior length of the heart. FIG. 35 illustrates the native mitral valve leaflets in an open condition, with the A2 portion of the anterior leaflet and the P2 portion of the posterior leaflet labeled. FIG. 35 illustrates a simplified cross-sectional representation of the guide catheter 5000. In particular, the guide catheter 5000 illustrated in FIG. 35 may be a portion of the guide catheter 5000 similar to the positioning catheter 4020, having been advanced from the guide catheter 5000 shown in FIG. 34 through the native mitral valve annulus. It should be understood that guide catheter 5000 can contain additional components, as described within this disclosure, such as a positioning catheter, an anchor catheter, a needle, etc. Further illustrated in FIG. 35 are two dotted lines roughly intersecting in a perpendicular manner. For example, the dotted line extending generally in the "x" direction illustrated in FIG. 35 may extend between the two commissures adjoining the anterior leaflet to the posterior leaflet. The dotted line extending generally in the "y" direction illustrated in FIG. 35 may extend between a center area of the A2 portion of the anterior leaflet and a center area of the P2 portion of the posterior leaflet. These dotted lines may also illustrate paths along which a guide catheter, e.g. guide catheter 5000, may be moved to palpate or otherwise touch anatomic landmarks in an effort to determine the central area of the mitral valve annulus, as described in greater detail below. These paths may include movement between an anterior to posterior position, and/or between a medial to lateral position.

In an embodiment, a method of determining a central portion of the native mitral valve annulus may begin with gaining transseptal access into the left atrium and advancing a guide catheter into the left atrium, such as guide catheter 5000. Once the guide catheter 5000 is in the left atrium, a distal tip may be deflected, for example using pull wires similar to those described above, to angle the distal opening of the guide catheter 5000 in general alignment with the center of the native mitral valve annulus, similar to the positions shown in FIGS. 33-34. Imaging techniques, such as echocardiography and/or fluoroscopic imaging, may be used in conjunction with the method. For example, an anchor or positioning catheter, which may be similar to anchor catheter 1200 of guide catheter 1000, may then be advanced from the guide catheter 5000 such that the anchor catheter extends into, and is surrounded by, the mitral valve annulus. Imaging techniques, such as echocardiography, may be used to help ensure that this step is performed correctly. The method may further include moving the anchor catheter, while it traverses the mitral valve annulus, in a lateral direction until contact with a commissure of the mitral valve annulus is made. The method may then include of moving the guide catheter in a medial direction until contact with the other commissure of the mitral valve annulus is made. In other words, referring to FIG. 35, the anchor catheter may be first moved to contact a first commissure, and then moved along the pathway extending in the "x" direction of FIG. 35 until the second commissure is contacted. Through measurement of the distance between contact between the commissures in the medial and lateral directions, and measured on for example, the x-y coordinate system illustrated in FIG. 35, an approximate center can be found in the 'x' direction by dividing this distance in half. This can be achieved via tactile feedback, in which the user feels when contact is made between the anchor catheter and the commissures. Similarly, to find the center in the 'y' direction of the x-y coordinate system of FIG. 35, the centers of the anterior and posterior leaflets can be touched by the anchor catheter, by moving the catheter along the dotted path extending in the "y" direction of FIG. 35. The distance between those two points may be measured, and the measured distance can be divided in half to determine where the general center of the mitral valve annulus is. By finding such a central position, and positioning the anchor catheter at said central position, the anchor catheter is positioned roughly at the center of the mitral valve annulus. As noted above, this central positioning may be desired in order to advance the anchor catheter toward the desired apical incision point along a direction that is substantially coaxial with the central longitudinal axis of the native mitral valve annulus. While some or all of the above-described steps of determining a center of the mitral valve annulus can be performed using tactile feedback, it should be understood that imaging techniques may also be used in conjunction with this method to provide more accurate results. It should further be understood that the techniques above can be performed by any catheter which may be nested within the positioning catheter.

Figure 36:
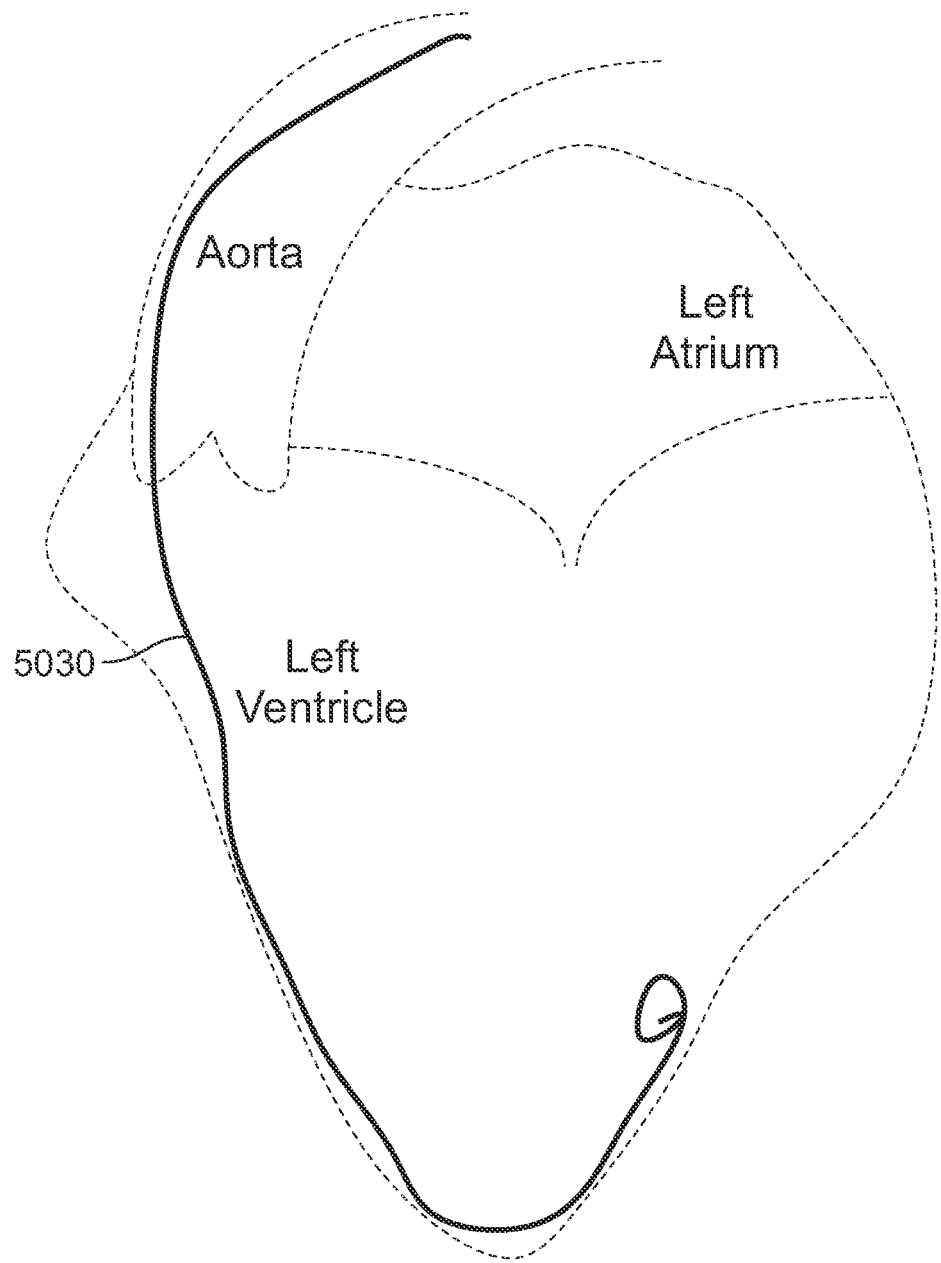
FIG. 36 illustrates a highly schematic view of a heart and instrumentation used during a valve replacement procedure as seen under fluoroscopy.

FIG. 36 illustrates other aspects of a method which can be used to align a catheter for use in creating the apical incision at the desired location and using the desired trajectory. FIG. 36 illustrates a guide wire 5030. In the embodiment illustrated in FIG. 36, the guidewire is advanced toward the apex of the left ventricle, and then back up along the interior left ventricular wall toward the left atrium, without actually passing into the left atrium. The guidewire may be a traditional guidewire, and may include a rounded or pigtail distal tip to reduce the likelihood of causing any unintentional trauma to the tissue contacted by the distal end of the guidewire. The guidewire may have enough flexibility so that the trajectory achieved by insertion of the guidewire through the aorta would allow for the guidewire to closely follow the interior contours of the left ventricle. Transfemoral introduction of the guidewire may be preferred to transseptal introduction, as the pathway achieved via this route is more likely to allow the guidewire to follow the contours of the left ventricle. Thus, when the guidewire is viewed under fluoroscopy, the guidewire may closely outline the shape of the interior walls of the left ventricle to provide the surgeons an indication of the shape of the interior of the left ventricle. Geometry information obtained in this manner can be compared to the pre-operative information to confirm that the planned catheter trajectory is suitable for the actual anatomical landscape encountered during the procedure.

Figure 37:
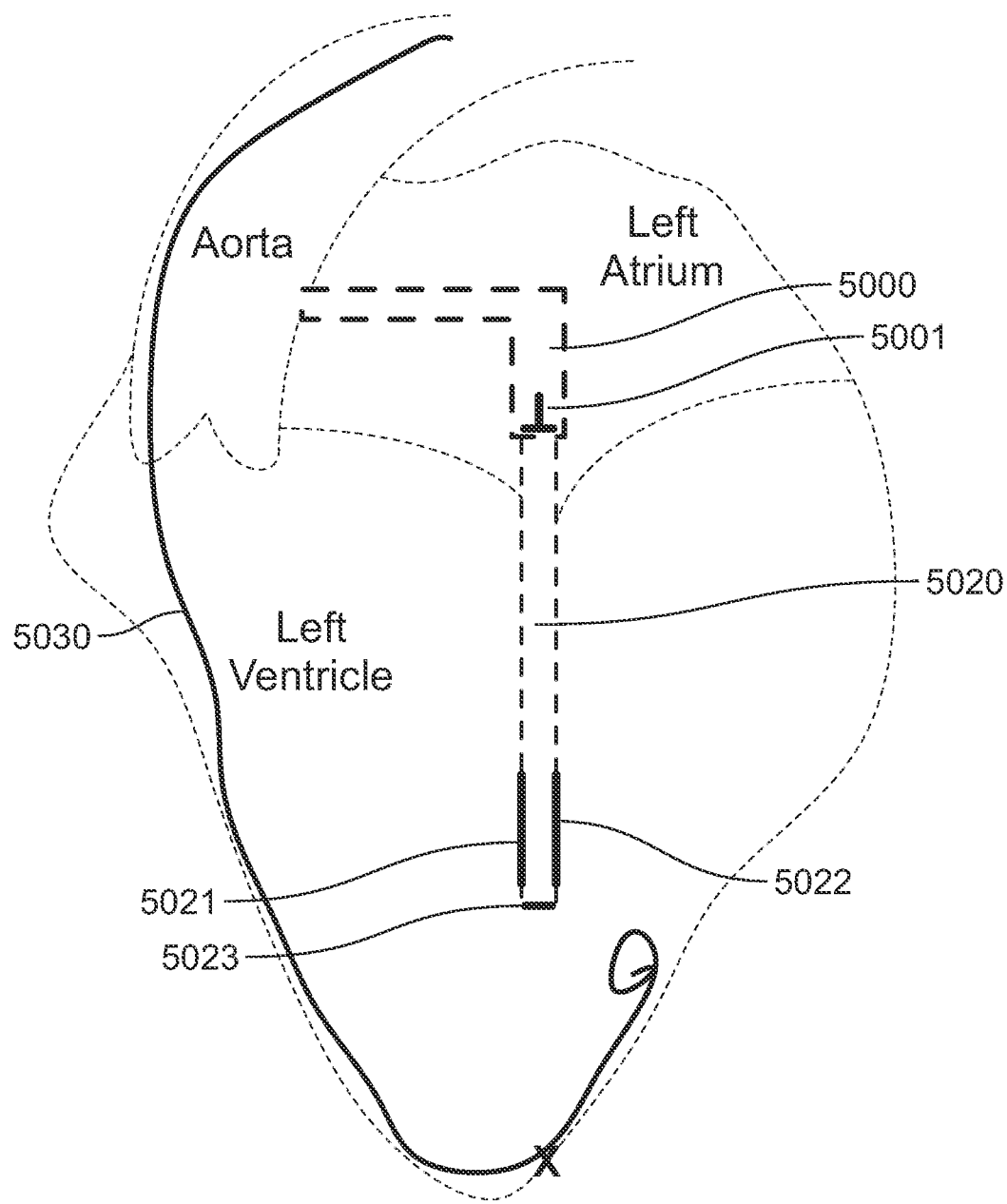
FIG. 37 illustrates another view of a heart and instrumentation used during a valve replacement procedure as seen under fluoroscopy.

FIG. 37 illustrates other aspects of a method which can be used to align a catheter for use in creating the apical incision at the desired location and using the desired trajectory. Illustrated in FIG. 37 is catheter 5000, an indicium 5001 on catheter 5000, a second catheter 5020, indicium 5021, indicium 5022, and indicium 5023 on catheter 5020, and a guide wire, 5030. Illustrated in solid lines within FIG. 37 are components which are clearly visible during fluoroscopy. Catheter 5020 may be a guide catheter such as guide catheter 4020 or anchor catheter 4099 described above. The description that follows may be performed alone, or in conjunction with the above method that first helps position the anchor catheter within the rough center of the mitral valve annulus. For example, as shown in FIG. 37, the method can further include the use of fluoroscopic image marking techniques to verify the trajectory derived from the steps above. Prior to the valve replacement procedure, the approximate location of the desired location for the apical puncture may be generally known. It may be difficult to confirm the desired positioning and trajectory using echocardiography imaging only, as such imaging procedures may not provide sufficient clarity to verify that the catheter is aligned properly to take the desired path during the procedure while the catheter is located within the heart. This can happen as catheters are generally made of polymers which are difficult to see with a high level of clarity when using echocardiography. However, the same catheter can be more clearly seen and imaged in higher detail when viewed through fluoroscopy, particularly when the catheter is marked or lined with indicia with high visibility under fluoroscopy, such as metallic markers. In order to more clearly verify the desired positioning under fluoroscopy, a guide wire may be inserted into the left ventricle in order to outline the left ventricle. As described with reference to FIG. 36 and FIG. 37, for example, a metallic guide wire, such as guide wire 5030 can be introduced through transfemoral access, tracked around the aortic arch, passed through the native aortic valve, and inserted further into the left ventricle. It should be understood that imaging under contrast media may be used in some circumstances to provide relevant anatomical information that could also be used to confirm the desired trajectory, but it is generally preferable to avoid using contrast if possible, as contrast media may result in additional procedural complications.

FIG. 37 illustrates a simplified view of a heart and instrumentation used during a valve replacement procedure when seen in a fluoroscopic view. In FIG. 37, dashed lines indicate soft tissue of the anatomy and polymeric or other non-metallic instrumentation components which may generally have low visibility under fluoroscopic imaging. In FIG. 37, solid lines indicate metallic materials or other materials that are highly visible under fluoroscopic imaging. A first indicium, such as indicium 5001 shown in FIG. 37 is an inverted "T" shape fluoroscopic marker near a distal end of the guide catheter 5000. The inverted "T" shape may include a first line that is generally parallel to the distal tip of the guide catheter, with a second line that is orthogonal or perpendicular to the first line and extending parallel to a longitudinal axis of the guide catheter. Indicium 5001 may be viewed under fluoroscopy after the distal end of the guide catheter has been deflected toward the mitral valve annulus in order to confirm desired positioning relative to other features viewed under fluoroscopy, described below. Second indicia shown in FIG. 37 includes three lines on the guide catheter or anchor catheter, including two lines extending along opposing sides of the anchor catheter in a direction parallel to one another and parallel to the longitudinal axis of the anchor catheter, with the longitudinal axis of the anchor catheter being positioned between the two marker lines. The third marker line may include a line adjacent the distal end of the anchor catheter, extending in a direction substantially parallel to the distal end of the anchor catheter, perpendicular to the two parallel lines, and extending generally between those two parallel lines. The guidewire described above, which is shown following the outline of the ventricle, is also visible in the fluoroscopic image represented in FIG. 37. Collectively, the guide wire and the fluoroscopic markers outline the shape of the ventricle and the location and orientation of the guide catheter 5000 and the anchor catheter. The first indicium may be compared to the second indicium and the outline of the guidewire in order to confirm that the anchor catheter is extending in the desired trajectory and at the desired position relative to the position of the guide catheter 5000 and relative to the pre-determined location of the apical incision, the position of the predetermined apical incision being determined at least in part using the outline of the guidewire that represents the outline of the ventricle. The pre-determined location of the apical incision is illustrated in FIG. 37 is a stylized "X" near the pericardium. If the fluoroscopic imaging indicates that the catheter is not positioned to perform the apical incision at the desired location and along the desired trajectory, the catheter(s) may be steered until the catheters are in the desired position. Then, a needle or similar structure within the catheter may be advanced to begin the process of creating the apical incision, and that procedure may be similar or identical to apical incision described above. Although the shapes and positions of the various fluoroscopic indicia are illustrative, any suitable markers, shapes, or indicia can be used to achieve and carry out the methods and procedures described herein.

The methods can further consist of, or be used in conjunction with the steps of steering a catheter to be aligned with the pre-determined poke location.

An example method can consist of the any combination of the steps of: (i) inserting, transseptally, a guide catheter into the left atrium; (ii) advancing, transseptally, the guide catheter; (iii) advancing the positioning catheter, contained within the guide catheter, to be surrounded by the mitral valve; (iv) obtaining a central location, approximated by half the distance between the lateral and medial commissures in one dimension, and half the distance between the anterior and posterior leaflets, by moving the guide catheter to said points and obtaining a tactile response; (v) moving the guide catheter to said central location; (vi) inserting, transfemorally, a guide wire through the aorta; (vii) viewing said guide wire to indicate outline and obtain a ventricle geometry; (viii) viewing fluoroscopically, indicia on a guide catheter, positioning catheter, and/or anchor catheter, to determine positioning information; (ix) aligning catheter(s) with a pre-determined poke point through steering of catheter; (x) extending catheter(s) to create a puncture at substantially the pre-determined poke point; (xi) extending the pad from the anchor catheter through the puncture; (xii) collapsing, into the guide catheter, one or more catheters; removing, transseptally the guide catheter; (xiii) removing, transfemorally, the guide wire. The method described above is not limited, and can be modified with other apparatuses, techniques, and additional steps to obtain the results indicated.

As should be understood from the above description, the devices and methods described herein may allow for an epicardial anchor or similar device to be positioned on an outer surface of the heart (or within the pericardium) without creating any incisions in the patient's chest. Thus, both a prosthetic heart valve and an anchoring device for that prosthetic heart valve may be delivered in a fully transcatheter manner. This may both reduce complexity of the overall procedure, reduce risks to the patient, and reduce recovery time for the patient.

According to one aspect of the disclosure, a delivery catheter system comprises:
  a guide catheter,
  an anchor catheter,
  a collapsible and expandable anchor for anchoring a prosthetic heart valve in a native heart valve, the anchor configured to be received within the anchor catheter,
  a balloon formed along a length of the guide catheter, the balloon being inflatable via a lumen in fluid communication with the balloon, and/or
  a needle positioned radially inward of the guide catheter and translatable relative to the balloon, the needle having a sharp distal tip, and/or
  the balloon is positioned a spaced distance from a distal end of the guide catheter, and/or
  the needle is solid, and/or
  the needle is hollow, and/or
  the guide catheter is steerable via at least one pull wire, and/or
  a positioning catheter positioned radially outward of the anchor catheter, the anchor catheter being translatable relative to the positioning catheter, and/or
  a spring element positioned between the balloon and a distal end of the guide catheter, the spring element biasing the guide catheter toward a straight condition, and/or
  at least one pull wire and the spring element are positioned on substantially opposite sides of the guide catheter, so that pulling the at least one pull wire tends to flex or compress the spring element, and/or
  at least one pull wire and the balloon are positioned on substantially opposite sides of the guide catheter, so that pulling the at least one pull wire tends to flex the distal end of the guide catheter away from the balloon.

According to another aspect of the disclosure, a method of delivering an expandable prosthetic heart valve anchor to a heart of a patient comprises:
  advancing a guide catheter into a left atrium of the patient, the guide catheter including a balloon formed along a portion of the guide catheter,
  advancing an anchor catheter from within the guide catheter to a left ventricle of the heart of the patient, the anchor catheter configured to maintain the anchor in a collapsed condition,
  inflating the balloon so that the balloon contacts an interior wall of the left atrium;
  advancing a needle positioned radially within the anchor catheter distally relative to the anchor catheter and through a ventricular wall of the heart of the patient to create a transapical puncture while the balloon contacts the interior wall of the left atrium, and/or
  advancing the anchor catheter at least partially through the transapical puncture; and
  releasing the anchor from the anchor catheter and allowing the anchor to transition from the collapsed condition to an expanded condition while the anchor catheter is positioned at least partially through the transapical puncture, and/or
  inflating the balloon is performed after the anchor catheter is advanced to the left ventricle, and/or
  deflecting a distal end of the guide catheter toward a native mitral valve annulus prior to advancing the anchor catheter into the left ventricle, so that the distal end of the guide catheter is substantially aligned with a central longitudinal axis passing through the native mitral valve annulus, and/or
  the balloon is formed of a compliant or semi-compliant material, and/or
  the balloon at least partially conforms to the interior wall of the left atrium after inflating the balloon, and/or
  the balloon remaining inflated against the interior wall of the left atrium after the needle is advanced through the ventricular wall and before the anchor catheter is at least partially advanced through the transapical puncture.

According to another aspect of the disclosure, a method of delivering an expandable prosthetic heart valve anchor to a heart of a patient comprises:
  advancing a guide wire through an aorta of the patient into a left ventricle of a patient; and/or
  advancing the guide wire substantially along an interior surface of the left ventricle such that the guide wire outlines at least a portion of the left ventricle; and/or
  advancing a guide catheter into a left atrium of the patient; and/or
  creating a transapical puncture in the heart by advancing a needle from the guide catheter along a trajectory through a ventricular wall of the patient, and/or
  the trajectory is determined at least partially based on an image of the guide wire under fluoroscopy and/or
  moving the guide catheter in a first direction substantially along a plane extending through an annulus of a native mitral valve to contact anterior and posterior leaflets of the native mitral valve to determine a first set of boundaries of the annulus, and/or
  moving the guide catheter in a second direction substantially along the plane extending through the annulus of the native mitral valve to contact commissures of the native mitral valve to determine a second set of boundaries of the annulus, and/or determining a center longitudinal axis of the annulus based on midpoints of the first and second sets of boundaries, and/or the guide catheter includes indicia visible under fluoroscopy, and/or the indicia on the guide catheter include a first marker substantially aligned with a longitudinal axis of the guide catheter, and a second marker substantially aligned with a distal end of the guide catheter, the first marker being substantially perpendicular to the second marker, and/or aligning the first marker with a longitudinal axis of a native mitral valve annulus prior to creating the transapical puncture in the heart, and/or the guide catheter includes an internal catheter positioned radially within the guide catheter, the internal catheter including second indicia visible under fluoroscopy, and/or the second indicia include a third marker substantially aligned with a longitudinal axis of the internal catheter, and a fourth marker substantially aligned with a distal end of the internal catheter, the third marker being substantially perpendicular to the fourth marker, and/or advancing the internal catheter distally relative to the guide catheter while viewing an orientation of the second indicia relative to the first indicia under fluoroscopy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of delivering an expandable anchor for a prosthetic heart valve to a heart of a patient, the method comprising:
    advancing a guide wire through an aorta of the patient into a left ventricle of a patient;
    advancing the guide wire substantially along an interior surface of the left ventricle such that the guide wire outlines at least a portion of the left ventricle;
    advancing a guide catheter into a left atrium of the patient; and
    creating a transapical puncture in the heart by advancing a needle from the guide catheter along a trajectory through a ventricular wall of the patient,
    wherein the trajectory is determined at least partially based on an image of the guide wire under fluoroscopy.

2. The method of claim 1, further comprising:
    moving the guide catheter in a first anterior-to-posterior direction substantially along a plane extending through an annulus of a native mitral valve to contact anterior and posterior leaflets of the native mitral valve to determine a first set of boundaries of the annulus.

3. The method of claim 2, further comprising:
    moving the guide catheter in a second direction substantially along the plane extending through the annulus of the native mitral valve to contact commissures of the native mitral valve to determine a second set of boundaries of the annulus.

4. The method of claim 3, further comprising:
    determining a center longitudinal axis of the annulus based on midpoints of the first and second sets of boundaries.

5. The method of claim 1, wherein the guide catheter includes indicia visible under fluoroscopy and the indicia on the guide catheter includes a first marker substantially aligned with a longitudinal axis of the guide catheter, and a second marker substantially aligned with a distal end of the guide catheter, the first marker being substantially perpendicular to the second marker.

6. The method of claim 5, further comprising aligning the first marker with a longitudinal axis of a native mitral valve annulus prior to creating the transapical puncture in the heart.

7. The method of claim 6, wherein the guide catheter includes an internal catheter positioned radially within the guide catheter, the internal catheter including second indicia visible under fluoroscopy.

8. The method of claim 7, wherein the second indicia include a third marker substantially aligned with a longitudinal axis of the internal catheter, and a fourth marker substantially aligned with a distal end of the internal catheter, the third marker being substantially perpendicular to the fourth marker.

9. The method of claim 8, further comprising:
    advancing the internal catheter distally relative to the guide catheter while viewing an orientation of the second indicia relative to the first indicia under fluoroscopy.

* * * * *